(12) United States Patent
Clarkson

(10) Patent No.: US 10,527,591 B2
(45) Date of Patent: Jan. 7, 2020

(54) SYSTEM AND METHOD FOR ANALYSIS OF FIBRE REINFORCED COMPOSITES

(71) Applicant: UT Comp Inc., Cambridge (CA)

(72) Inventor: Geoffrey E Clarkson, Cambridge (CA)

(73) Assignee: UT COMP INC., Cambridge, ON (CA)

( * ) Notice: Subject to any disclaimer, the term of this patent is extended or adjusted under 35 U.S.C. 154(b) by 0 days.

(21) Appl. No.: 15/996,786

(22) Filed: Jun. 4, 2018

(65) Prior Publication Data

US 2018/0348172 A1  Dec. 6, 2018

Related U.S. Application Data

(63) Continuation of application No. 14/882,570, filed on Oct. 14, 2015, now Pat. No. 9,989,502.

(60) Provisional application No. 62/063,568, filed on Oct. 14, 2014.

(51) Int. Cl.
  *G01N 29/04* (2006.01)
  *G01N 29/44* (2006.01)

(52) U.S. Cl.
  CPC ....... *G01N 29/4427* (2013.01); *G01N 29/043* (2013.01); *G01N 2291/0231* (2013.01); *G01N 2291/102* (2013.01)

(58) Field of Classification Search
  CPC ........... G01N 29/043; G01N 2291/102; G01N 2291/0231
  USPC .......................................................... 73/588
  See application file for complete search history.

(56) References Cited

U.S. PATENT DOCUMENTS

| | | | |
|---|---|---|---|
| 5,907,100 A * | 5/1999 | Cook | G01N 29/2412 73/602 |
| 9,002,022 B1 * | 4/2015 | Clemen, Jr. | H04R 29/00 310/334 |
| 9,581,529 B2 * | 2/2017 | Hesse | G01N 3/08 |
| 2002/0029647 A1 * | 3/2002 | Brooks | B60K 17/04 74/424 |
| 2008/0148854 A1 * | 6/2008 | Georgeson | G01N 29/11 73/599 |
| 2009/0049920 A1 * | 2/2009 | Young | G01N 29/07 73/649 |

* cited by examiner

Primary Examiner — Jacques M Saint Surin
(74) Attorney, Agent, or Firm — Gowling WLG (Canada) LLP; Neil W. Henderson

(57) ABSTRACT

A system for analyzing fiber reinforced composite including: an ultrasonic transmitter configured to provide ultra-sonic pulses to the fiber reinforced composite; an ultrasonic receiver configured to receive ultrasonic signal data related to the ultrasonic pulses; a filter module configured to filter the ultrasonic signal data; a signal processing module configured to process the filtered ultrasonic signal data; an analysis module configured to analyze the processed ultrasonic signal data by: calculating a characteristic value based on the ultrasonic signal data; comparing the characteristic value to a baseline established for the characteristic value; and determining a percentage of design strength based on the comparison; and an output module configured to output the percentage of design strength.

18 Claims, 25 Drawing Sheets

$L_t$ vs Normalized Strength Percentage $L_{tt}$ vs Normalized Strength Percentage (c) $V$ vs Normalized Strength Percentage (d) $LV$ vs Normalized Strength Percentage

SYSTEM AND METHOD FOR ANALYSIS OF FIBRE REINFORCED COMPOSITES

RELATED APPLICATIONS

This application is a continuation of U.S. patent application Ser. No. 14/882,570 filed Oct. 14, 2015, which claims the benefit of U.S. Provisional Patent Application No. 62/063,568 filed Oct. 14, 2014, the content of which is incorporated herein by reference.

FIELD

The application relates to a system and method for analysis of fiber reinforced composites.

BACKGROUND

Ultrasonic readings taken from fiber reinforced composites, such as plastics, can be related to the elastic modulus, and hence the strength of the material. Research results dating back to the 1960's have shown that stressing fiberglass reinforced polymers (FRP) may result in decreasing the modulus of the material—thus reducing its strength. In service, the stresses applied to FRP typically have the same effect.

An early patent application regarding use of ultrasound for testing materials was made in 1940 by Dr. Floyd Firestone at the University of Michigan. This early patent, and most subsequent work using ultrasound identified that invisible inhomogeneities within materials could be detected. For most of the 74 years since this patent application, the focus of ultrasonic testing has been on metals. In the case of ultrasound, a pressure pulse is applied to a metal material and inhomogeneities are detected when a feature blocks some of the path of the ultrasounds—features that are parallel to the path direction are generally not detected.

Use of fiber reinforced composites for structural applications has been pursued since the 1930's, and has seen significant changes in the polymers and fibers available. With the growth of commercial aircraft starting in the 1960's, many investigations were conducted into use of ultrasound to detect flaws and defects in composites. Because many fiber reinforced composites are made in layers, interfaces between layers often interrupt the path of the pressure pulses and show as features or possible defects for most ultrasonic techniques. Ultrasound is generally considered to be the most common non-destructive technology used for composite materials.

In the early 1960's, use of ultrasonic testing (UT) was already showing reliable results for finding flaws in metallic structures. One of the desirable attributes of this technique is that reliable data could be generated if only one side of the material under investigation was accessible. This meant that in addition to finding flaws or defects, the same techniques could be used to produce thickness records of reasonable accuracy. At the same time, use of composite materials such as glass reinforced thermoset plastics was being explored for a number of structural and corrosion-resistant applications. Starting in the mid 1960's, researchers started to examine uses of ultrasound with these fiber-reinforced composite materials.

In one study, ultrasonic pulses were applied to composites and the responses were received using acousto-ultrasonic devices, thus mixing the principles of ultrasound with acoustic emission testing. This process is generally referred to as "acousto-ultrasonic" because the forces applied to the specimen are from ultrasonic pulses, whereas for acoustic emission, the forces applied to the composite are from mechanical loads, such as pressures and weights. In both cases, the responses are received in real time by acoustical equipment. This work showed correlation between the attenuation of the signal transmitted through the full thickness of a laminate—across its layers—and its tensile strength parallel to its layers. This technique is the subject of two American Society for Testing and Materials (ASTM) standards—ASTM E 1495 Standard Guide for Acousto-Ultrasonic Assessment of Composite, Laminates and Bonded Joints[2] (ASTM E 1495) and ASTM E 1736 Standard Practice for Acousto-Ultrasonic Assessment of Filament Wound Pressure Vessels[3] (ASTM E 1736).]

A method to employ these techniques is described in ASTM E 1736. In this Standard Practice, it is recommended that initial readings be taken from the vessel to be monitored after calibration to a reference standard and before it is put into service. After the unit has been in service for some time, the results of the initial readings are then compared to readings taken after the unit has been in service. Changes that have occurred in the modulus of the composite from corrosion, decay or mechanical loads will appear as changes in the results of the scan. While there is a relationship between acousto-ultrasonic results and the presence of detectable defects such as voids or delaminations and porosity, it is not certain as yet whether or not these defects are the cause of strength changes. Furthermore, in order to make use of any correlation, it is generally required that reference standards be available for each feature and condition that requires detection.

Many users of structural composites can report that the structural capacity of the composite has reduced while it has been in service. There have been numerous investigations into this phenomenon, including proposed models of the causes of these changes.

Embodiments of the system and method described herein are intended to address at least one of the drawbacks of conventional systems and methods.

SUMMARY

In a first aspect, the present disclosure provides a system for analyzing fiber reinforced composite, the system including: an ultrasonic transmitter configured to provide ultrasonic pulses to the fiber reinforced composite; an ultrasonic receiver configured to receive ultrasonic signal data related to the ultrasonic pulses; a filter module configured to filter the ultrasonic signal data; a signal processing module configured to process the filtered ultrasonic signal data; an analysis module configured to analyze the processed ultrasonic signal data by: calculating a characteristic value based on the ultrasonic signal data; comparing the characteristic value to a baseline established for the characteristic value; and determining a percentage of design strength based on the comparison; and an output module configured to output the percentage of design strength.

In a particular case, there is provided a memory component configured to store ultrasonic signal data and baseline for characteristic values.

In another particular case, the filter module is configured to extract relevant data from the ultrasonic signal data.

In still another particular case, the relevant data includes data associated with the material being tested and the extracted data includes data associated with the ultrasonic transmitter and the ultrasonic receiver.

In yet another particular case, the relevant data includes a magnitude of a reflection from the opposite surface of the fiber reinforced composite.

In still yet another particular case, the output module is further configured to output a projection of a time remaining prior to a predetermined threshold value is reached.

In a particular case, the predetermined threshold value is a value related to a replacement requirement.

In still another particular case, the output module is configured to output data related to a strength level of a bonding at joins of the fiber reinforced composite.

In another aspect, there is provided a method for analyzing fiberglass reinforced polymer, the method including: taking ultrasonic signal data from the fiber reinforced composite; receiving the ultrasonic signal data, at an ultrasonic receiver; filtering the ultrasonic signal data, at a filter module; processing the filtered ultrasonic signal data, at a signal processing module; analyzing the processed ultrasonic signal data, at an analysis module, wherein the analysis comprises: calculating a characteristic value based on the ultrasonic signal data; comparing the characteristic value to a baseline established for the characteristic value; and determining a percentage of design strength based on the comparison; and displaying the percentage of design strength of the fiber reinforced composite, at an output module.

In a particular case, the method further includes storing the ultrasonic signal data and baseline for characteristic values at a memory component.

In another particular case, the filtering of the ultrasonic signal data includes extracting relevant data from the ultrasonic signal data.

In still another particular case, relevant data includes data associated with the material being tested and the extracted data includes data associated with the ultrasonic transmitter and the ultrasonic receiver.

In yet another particular case, the relevant data includes a magnitude of a reflection from the opposite surface of the fiber reinforced composite.

In still yet another particular case, the method includes displaying a projection of a time remaining prior to a predetermined threshold value is reached.

In another particular case, the predetermined threshold value is a value related to a replacement requirement.

In yet another particular case, the method includes displaying data related to a strength level of a bonding at joins of the fiber reinforced composite.

Other aspects and features of the present disclosure will become apparent to those ordinarily skilled in the art upon review of the following description of specific embodiments on conjunction with the accompanying figures.

BRIEF DESCRIPTION OF THE DRAWINGS

Embodiment of the present disclosure will now be described by way of example only, with reference to the attached Figures.

DETAILED DESCRIPTION

Figure 1:
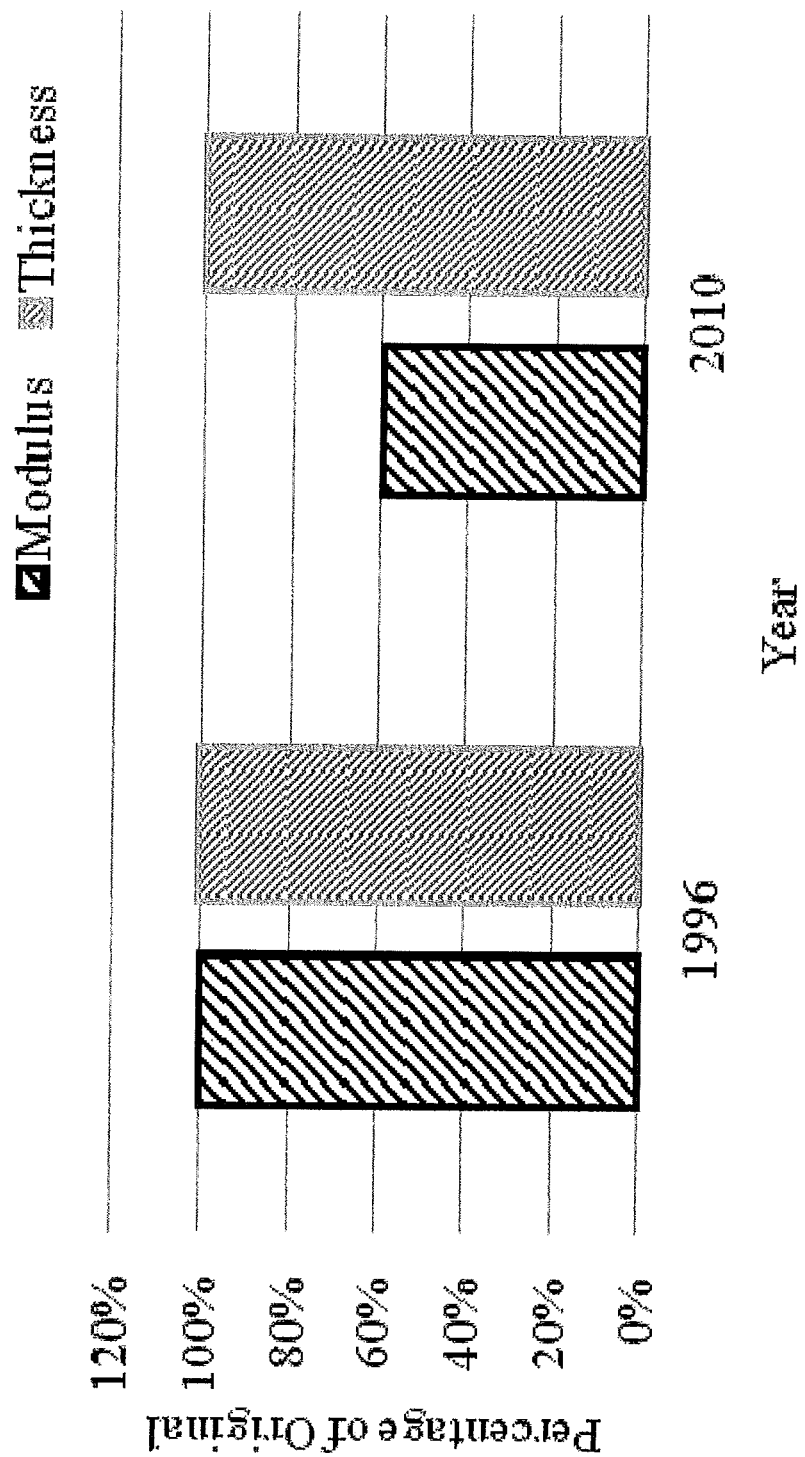
FIG. 1 illustrates destructive test results from samples removed from glass fiber reinforced tank shell.

Conventional research has been successful in identifying that changes in fiber reinforced composites (FRC) (such as fiber reinforced polymers, fiber reinforced plastics, fiberglass reinforced composites, fiberglass reinforced polymers, or the like) for example reduced strength or elastic modulus, occur over time. Reduction in structural capacity has not been universally associated with any change in defects that are normally detected by ultrasonic methods, such as voids, delaminations or porosity within the composites. It is most common for defects and discontinuities to be widely dispersed and not identified as discrete flaws.

In some cases, ultrasonic pulses may be used to detect flaws or provide data related to fiber reinforced composites. Ultrasonic pulses can be applied to materials in three main modes:
  pulse-echo, where the pulse is applied to the surface by the same transducer that receives reflected energy from within the material,
  thru-transmission, where the pulse is applied to one surface by one transducer and the pulses that pass through the material are received by a transducer placed on the opposite surface, and
  pitch-catch, where the pulse is applied to the surface by one transducer and another transducer on the same surface receives reflected energy within the material.

Ultrasonic pulses can generally range in frequency from approximately 100,000 Hertz (0.1 MHz) to beyond 20 MHz. When used with glass reinforced composite materials, signal losses in the material increase with frequency, making the highest reasonable frequency approximately 1.0 MHz. In the experiments detailed herein, a nominal ultrasound frequency of 500 kHz was used. In the experiments, attenuation values generally ranging from 0.3 to 2.0 decibels (dB)/mm (7.62 to 50.8 dB/in) were also used.

In ultrasonic testing, an energy pulse is applied to the face of a material by an ultrasonic device, for example, an actuator, a transducer, or the like. These pulses have a short wavelength which translates into a wave frequency in the range listed above. Ultrasound uses two primary modes to travel through a material—longitudinal and transverse waves. The experiments detailed herein used mainly longitudinal waves and fiber reinforced composites.

Currently, the most common use of longitudinal waves in FRC is in thickness measurement of new FRC structures. Thickness measurements are usually made by following this process:
1. A reference standard is used which duplicates the material to be measured with a known thickness so that the transit time of the reflected signal can be used to determine the sonic velocity through the reference standard
2. It is assumed that the sonic velocity through the material to be measured is the same as the reference standard.
3. The transit time of ultrasonic pulses applied to the material is converted into thickness.

Thickness testing generally does not use any other information contained in the returned ultrasound signal.

Flaws such as voids, porosity and planar defects that interrupt the path of the ultrasonic wave through a fiber reinforced composite will appear in an ultrasonic A-Scan and can often be analyzed by a skilled analyst. This principle is used for evaluating composites in some applications, aerospace in particular.

Propagation of sound waves through a medium is affected by changes along the wave path. Examples of these changes could be, for example, foreign objects, gaps or bubbles, changes in the structure of the material, or other changes. In the case of fiber reinforced composite materials, the structure of the material may include some (and sometimes all) of these changes along any wave path. These generally show as attenuation of any signal that passes through the material as well as visible indications on the test instrument. For glass reinforced composites, normal variations that occur because of materials and processes used may often be cause for rejection if using the same criteria that have been adopted for metals.

Several researchers have reported experimental results showing a correlation between the elastic modulus of FRC and acousto-ultrasonic results. This includes correlation of changes in strength that has occurred from applied stresses and chemical permeation, corrosion, or attack with changes in ultrasonic response of the FRC. These early researchers have successfully shown that acousto-ultrasonic methods can be used to determine general changes in condition of composite laminates.

It is important to note that the correlation does not mean that the value of the elastic modulus can be determined directly from the acousto-ultrasonic data. To determine the actual modulus it is generally necessary to know the modulus value corresponding to an acousto-ultrasonic value on at least one point along the curve. However, with the appropriate criteria, it is believed that this information can be used to determine whether a composite laminate is suitable for the loads to be applied in service conditions.

The central parameter measured by acousto-ultrasonic methods is termed the "stress wave factor" (SWF), which may be determined by counting the number of pressure pulses greater than a predetermined threshold value received by the sensor over a period of time, based on use of a calibration standard which came from the original, new composite. It is intended that the SWF from a composite can be used to determine the condition of the composite.

The embodiments of the system and method detailed herein use the output of ultrasonic flaw detection equipment to determine parameters that are used to calculate the condition of the composite. The output of the ultrasonic equipment appears as a generally static Cartesian graph, with time along the horizontal axis and overall magnitude on the vertical axis. The graph displayed is referred to as an "A-scan" and it may be configured to show the time series of signals received from pulses applied to the material.

The method, according to an embodiment herein, used to determine the state of the fiber reinforced composites, is configured to extract relevant data from the raw A-scan after various filters have removed data that is not associated with the actual material being tested, including data from within the transducer and instrument system. This data is identified both as a result of statistical analysis and from specific ultrasonic readings included in the process. This filtered A-scan then represents the net response of the material to the force from the ultrasonic pulse. One of the key parameters determined from the filtered A-scan is the magnitude of the reflection from the opposite surface, known herein as the Net Opposite Surface Reflection Magnitude (NOSRM). The method does not make use of calibration standards and the relevant data is obtained from the filtered A-scan.

FIG. 1 shows the results from tests of samples removed from a glass reinforced tank on two (2) occasions. The tank had been in service storing a corrosive liquid. The results shown are for the measured thickness of the tank shell and the results of destructive testing. The results of the tests are shown as percentages as given by equation (1) below.

$$\text{Percentage of Original} = \frac{\text{Current Measurement}}{\text{Original Measurement}} \times 100\% \quad (1)$$

From FIG. 1, it can be seen that during fourteen (14) years of service, the thickness of the laminate did not change appreciably but the modulus reduced by 40%. At some point in this decline, it is likely that the composite will no longer be able to support the required loads.

Two approaches are proposed for monitoring the condition of structural composites —one is to use a baseline developed from specimens of new FRC combined with theoretical work and the other is to use the results of ultrasonic readings taken from the new structure to be monitored and to use this as the baseline. Either approach is intended to address drawbacks of previous approaches.

Reliable performance of composites in structural applications, especially where remaining service life prediction is sought after, requires non-destructive methods that can verify structural properties including mechanical strength. Through the development of reliable non-destructive methods, regular evaluations can be completed to monitor condition. Such a system permits owners to avoid costly consequences (such as premature repair and replacement, confined space entry, environmental cleanup and lost opportunity) and capitalize on repeatable and reproducible information to manage repair and replacement scopes within budget cycles.

Developments in ultrasonic non-destructive evaluation of glass reinforced composites have generally been made using open-mold methods and laminate thickness of 6 mm and greater. Emphasis is on monitoring the condition of composites structures in service, using technology that has been developed and is described herein. One purpose of this disclosure is to describe an objective system and methodology for determining baseline values for use in monitoring changes occurring to composite structures in service.

Reliable performance of composites in structural applications, especially where life prediction is desired, requires non-destructive methods that can verify structural properties including mechanical strength. With availability of reliable non-destructive methods, regular evaluations can be completed to monitor condition.

At this writing, for industrial and civil applications there is not a generally accepted non-destructive methodology to determine whether a composite structure being put into service meets the design requirements. Furthermore, for composite structures that have been in service for some time, relevant non-destructive data is rarely available from the new structure, which prevents comparisons related to changes that have occurred and thus the determination of current suitability for service.

First, consider a parallel situation where a steel structure is to be evaluated. For steel, structural capacity is generally related directly to thickness. In this case, the original thickness is documented, say on a drawing or specification. Conventional non-destructive methods can be used to reliably determine the current thickness of the steel. It is reasonable to use the original documented thickness as the starting thickness, even if the actual thickness was different. From the starting thickness, the rate of thickness change can be determined and life prediction of the structure can be estimated, even when initial measurements might not be available.

Figure 2:
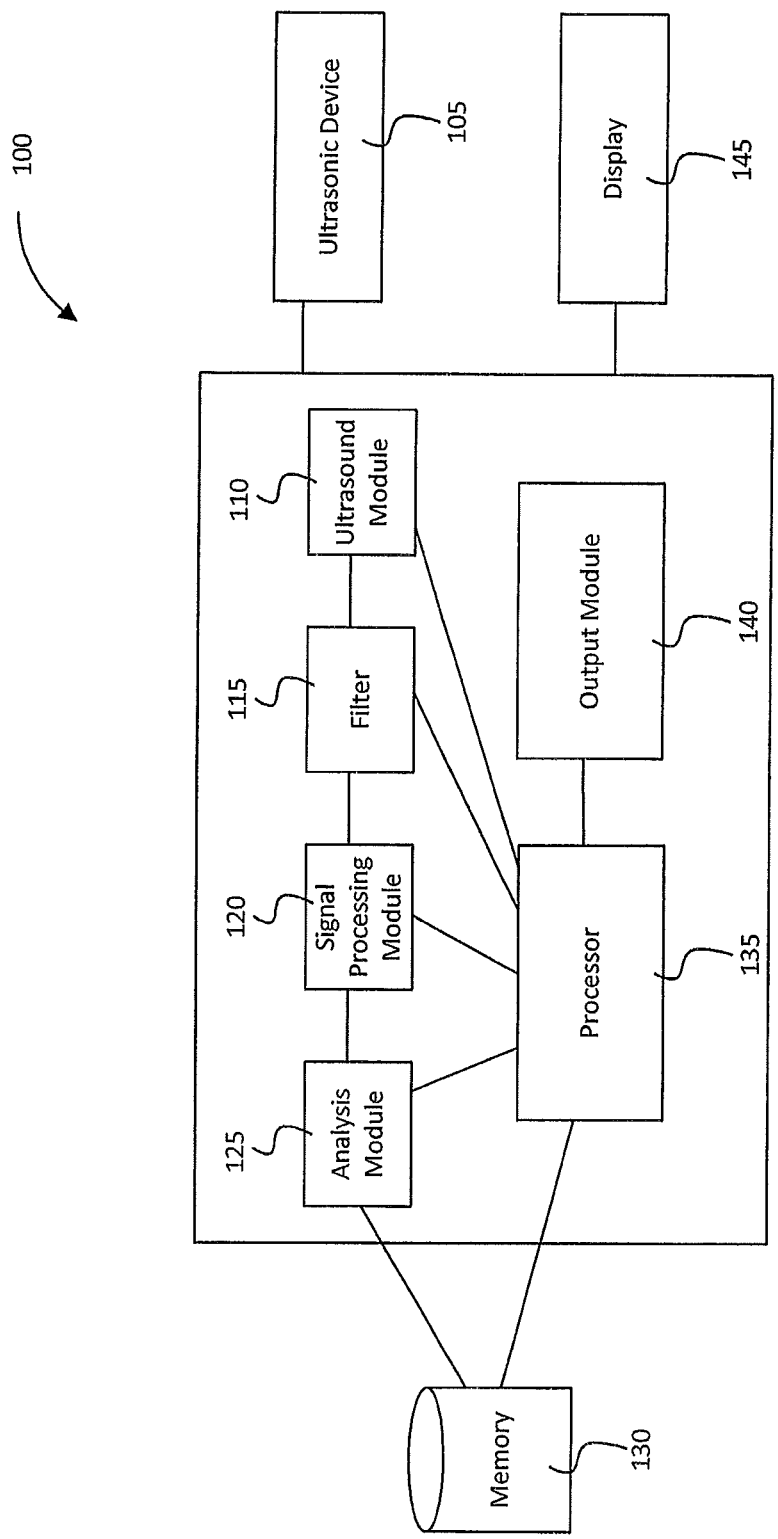
FIG. 2 illustrates an embodiment of a system for analyzing fiber reinforced composites.

FIG. 2 illustrates a system 100 for analyzing fiber reinforced composites. An ultrasonic device 105 is configured to provide ultra-sonic pulses to a fiber reinforced composites. The ultrasonic device 105 may be configured to receive readings, or ultrasonic signal data, and transfer readings to an ultrasonic module 110. In other cases, the ultrasonic module 110 may be configured to receive the ultrasonic readings directly.

The system 100 will generally include a filter module 115 configured to filter the ultrasonic readings. A signal processing module 120 will also generally be included and configured to process the ultrasonic readings prior to the analysis of the readings. In some cases, the filter module 115 and signal processing module 120 may be a single module.

The system 100 includes an analysis module 125 configured to analyze the ultrasonic readings. The analysis module 125 is configured to process the ultrasonic signal data, calculate a characteristic value based on the processing of the ultrasonic signal data, compare the characteristic value to a baseline established for the characteristic value, and determine a percentage of design strength based on the comparison. The normal characteristic value reported by the calculations is the percentage of the original flexural modulus of the composite. An output module 140 may be configured to receive the comparison and percentage of design strength and provide an output, for example a report, to a display 145.

A variety of outputs can be provided to provide information on the condition of the composite. For example, a primary report can provide details on the locations where ultrasonic readings were taken and may include a report of how the condition, in particular the flexural modulus of the composite, has changed during service life of the fiber reinforced composites. Based on the time-rate-of-change, a projection may be made of the remaining time until a specific value will be reached, for example: a predetermined replacement value, a risk level value or the like. Further outputs available may relate to the extent or strength of bonding at joints and the amount of damage that has occurred to portions of the composite that have been exposed to chemical environments.

A damage mechanism refers to changes that occur in a material that can lead to or predict failure. For fiber reinforced composites there are three (3) major damage mechanisms. Damage to the resin or matrix describes damage that can occur and accumulate in the resin due to conditions imposed on the composite. This damage can take the forms of microcracking and chemical changes to the resin. Damage to the reinforcement fibers can occur as chemical damage such as leaching elements from the glass or mechanical damage to the fiber, for example tensile fracture. Damage to the resin-fiber interface is damage that can occur to the bond between the fibers and the resin. Examples include chemical damage from corrosion or shear fracture of the bond. Damage mechanisms and failure modes, which are visible to the naked eye, are described as they are important for ongoing evaluation of the structural capacity of FRC.

The system 100 is further configured to include a memory component 130 configured to store data, such as, for example, baselines for characteristic values, thresholds, and the like. The system includes a processor 135, configured to execute the instructions or commands from the other modules.

Figure 3:
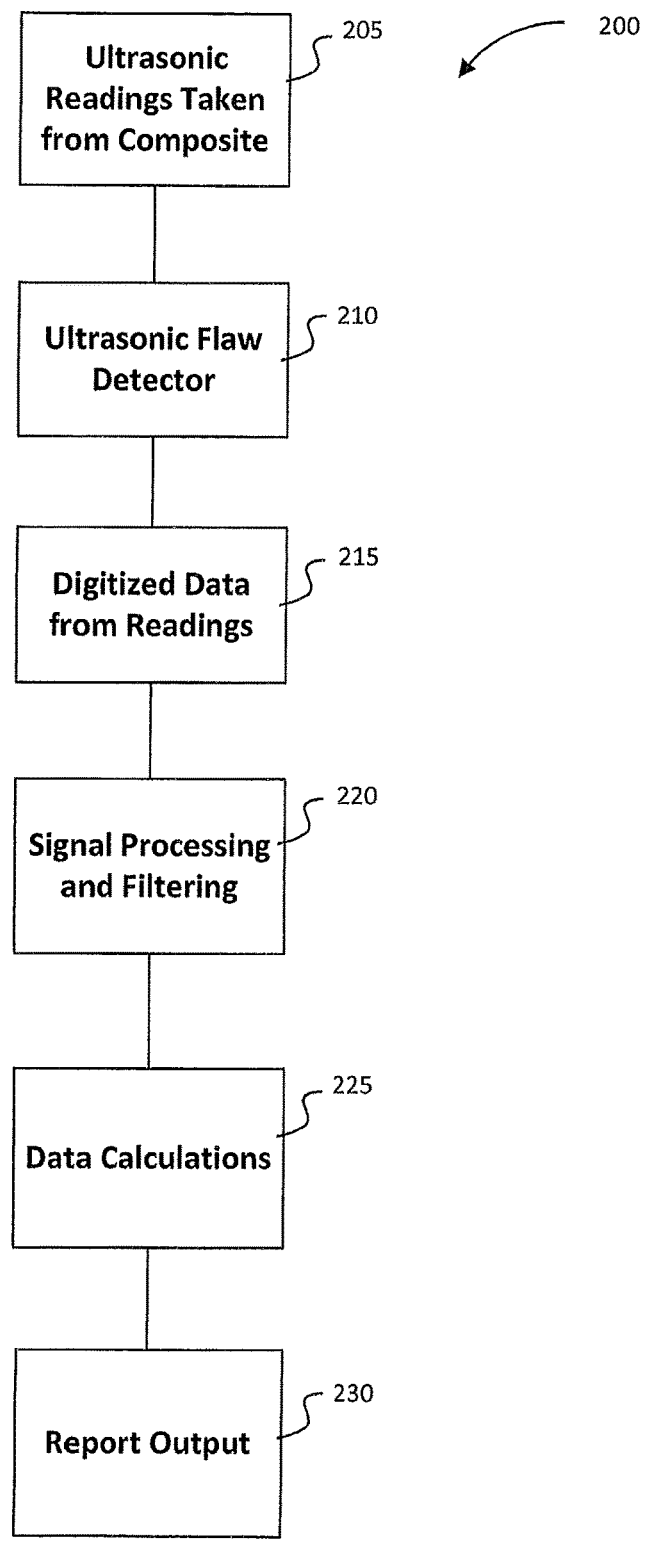
FIG. 3 illustrates an embodiment of a method for analyzing fiber reinforced composites.

FIG. 3 illustrates a method 200 for analyzing fiber reinforced composites.

At 205, ultrasonic readings are taken from the composite material. At 210, the ultrasonic module receives the readings related to detecting flaws in the material. At 215, the readings are digitized by the ultrasonic module 110.

At 220, the readings or signals are processed and filtered using the signal processing module 120 to convert all data to a consistent time and magnitude scale and the filtering module 115 to remove extraneous data created by external causes. At 225, data calculations are performed by the analysis module 125. The data calculations completed use the filtered results to determine the actual transit time and attenuation and are combined to produce the output values and at 230, the output module 140 provides a report or other output to the display 145.

Now consider a typical situation as shown in the case illustrated in FIG. 1, above, where thickness is not expected to change but the modulus does. In this case, non-destructive measurements similar to acousto-ultrasonic results described above are required to know the current relative modulus value. In order to create a prediction of the rate of modulus change, it will be necessary to have a starting value. For the purpose of this disclosure, the starting value, or "New" value, is the baseline value. It will be understood that other starting values may be used as a baseline value.

1. Experimentation

The work described herein was performed to develop a comparison between parameters calculated from ultrasonic readings and standard destructive test results for glass reinforced composite laminates.

1.1 Hypothesis

Ultrasonic data from a variety of glass reinforced composites can be used to establish a "universal" baseline parameter.

1.2 Experimental Method

To compare methods, samples of glass reinforced composites were produced, or removed from various structures, and tested both by the ultrasonic methods described herein and by using standard destructive tests to determine the modulus of the material. A total of thirty-six (36) samples were used. Thirty percent (30%) of the samples were newly made, and the remaining seventy percent (70%) had been in service for up to thirty (30) years.

The samples were constructed using open mold techniques and had varying reinforcement content. Twenty-five (25) samples were made using filament winding and ten (10) used contact molding. Each sample was approximately 300 mm×300 mm in size. Sample thicknesses ranged from eight (8) mm (0.315 inch) to forty-eight (48) mm (1.890 inches). Most of the samples were from cylindrical shells where the material properties in the hoop direction were of most interest.

The samples used for these experiments were manufactured by twelve (12) different manufacturers using different methods and practices. For the samples that were provided from structures exposed to corrosive substances, chemical attack and absorption was also different.

It is expected that differences among samples from these factors will also introduce random variation.

The designation of the destructive test used is ASTM D 790.

1.2.1 Non-Destructive Tests

The ultrasonic readings were taken by in the manner described below. All readings were pulse-echo readings using a 0.5 MHz transducer with a vulcanized rubber delay line. For each sample, the average thickness was measured using a caliper and recorded. At least 30 readings were taken over the surface of each sample.

The ultrasonic readings were then processed, via the filter module 115 and the signal processing module 120 to identify the opposite surface reflection and to calculate the value and total transit time of the reflected peak. Thickness was used to determine the average sonic velocity for the reading.

The results of all readings for a sample were averaged.

For each sample the following non-destructive parameters were calculated:

$$L = f(\text{attenuation}) = \frac{NOSRM}{(\text{Gross Attenuation by the Material Tested})^{0.25}} \quad (2)$$

$$L_t = L \times \text{thickness} \quad (3)$$

$$L_{tt} = L \times \text{transit time} \quad (4)$$

$$V = 2 \times \frac{\text{thickness}}{\text{transit time}} \quad (5)$$

$$LV = L_t \times V \quad (6)$$

The values calculated using (2), (3), (4), (5) and (6) were tabulated by sample.

1.2.2 Destructive Tests

For each of the samples, the procedure outlined below was followed:

1. Ultrasonic data and thickness measurements were collected from the sample.
2. The sample was cut into test specimens in accordance with ASTM D 790.
3. Where the lamination sequence of the sample was unknown, a specimen was also cut for ignition loss analysis in accordance with ASTM D 2584 and reinforcement analysis.
4. A third-party test laboratory completed the ASTM D 790 and ASTM D 2584 (as applicable) testing and reported the results.
5. The third party laboratory returned the reinforcement from the ASTM D 2584 specimen as it was removed from the furnace.
6. The ASTM D 2584 residue was used to determine the lamination sequence.
7. The Design Flexural Modulus was modeled using lamination analysis as described in ASME RTP-1.
8. The flexural modulus result obtained from the ASTM D 790 test was normalized by dividing it by the design values from lamination analysis modeling and termed "Normalized Strength Percentage" as in equation (6).

$$\text{Normalized Strength Percentage} = \frac{ASTM\ D\ 790\ \text{Modulus}}{\text{Design Flexural Modulus}} \times 100\% \quad (7)$$

An example of the calculation process is shown below:

TABLE 1

| Calculation Example | | | |
|---|---|---|---|
| Design Flexural Modulus in GPa (Msi) | Thickness in mm (in) | ASTM D 790 Modulus in GPa (Msi) | Normalized Strength Percentage |
| 15.36 (2.229) | 48.03 (1.891) | 9.25 (1.343) | 60.2% |

2. Results

2.1 Normalized Strength Percentage

Figure 4:
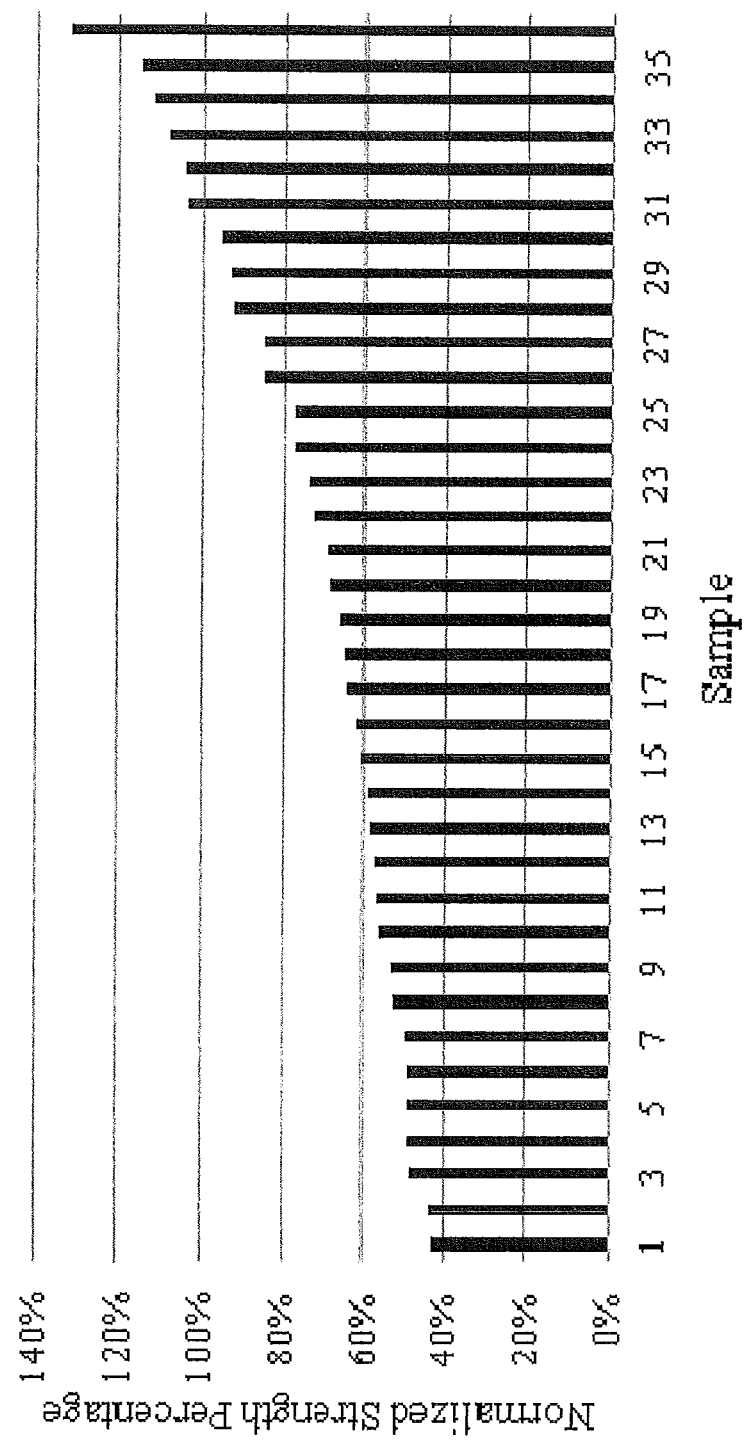
FIG. 4 illustrates normalized strength percentage results according to an example experiment.

The results of the normalized strength percentage calculations are presented in FIG. 4. The data have been ordered from highest to lowest. Note that the values range from 43% to 132% of the calculated design value.

2.2 Non-destructive Parameters

For all readings taken from each sample, the reflection of the applied pulse from the opposite surface was selected. Where the opposite surface reflection could not be identified, the reading was discarded.

The values listed in equations were calculated and averaged for the sample. The values of $L_t$, $L_{tt}$, V, and LV were then plotted with the corresponding normalized strength percentage as shown in FIG. 5 (a) to (d), below. The scatter of the data points is believed to be largely due to random variation introduced by differences among samples as discussed above.

Correlation coefficient and R-squared values for linear regression between the normalized strength percentage and the calculated values were calculated and are shown in Table 2.

TABLE 2

Correlations with Normalized Strength Percentage

| | Non-Destructive Parameter and Equation Number | | | |
|---|---|---|---|---|
| | $L_t$ (3) | $L_u$ (4) | V (5) | LV (6) |
| Correlation Coefficient | 0.871 | 0.827 | 0.365 | 0.898 |
| R-squared | 0.759 | 0.6833 | 0.133 | 0.806 |

From Table 2, the best correlation and linear regression results correspond with the LV value determined by equation 6. These data are shown in FIG. 5(d). Calculation of this value requires the magnitude and transit time of the opposite surface reflection from the ultrasonic readings as well as the thickness of the composite. If the thickness of the composite is unknown, the parameter $L_{tt}$ is the alternative, although with lower correlation.

2.3 Sonic Velocity Considerations

Figure 5A:
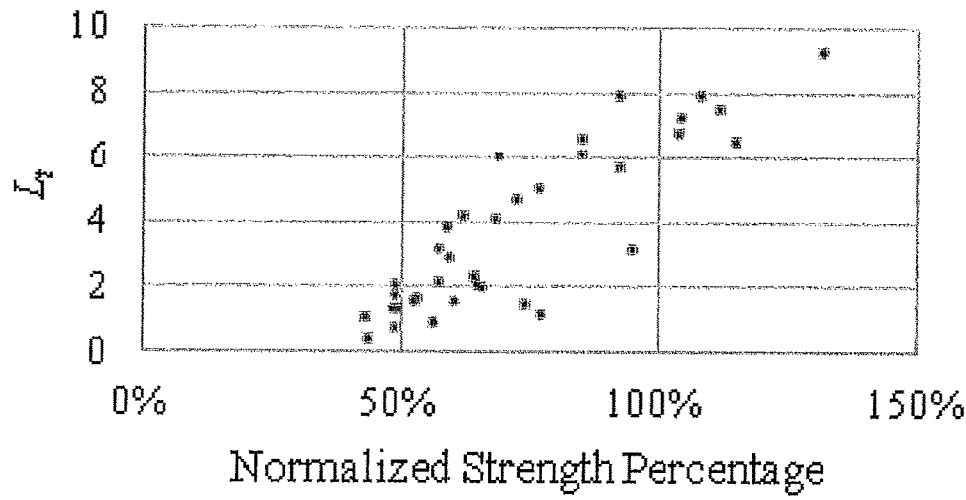
FIGS. 5A to 5D illustrates non-destructive parameters plotted against destructive test results.
Figure 5B:
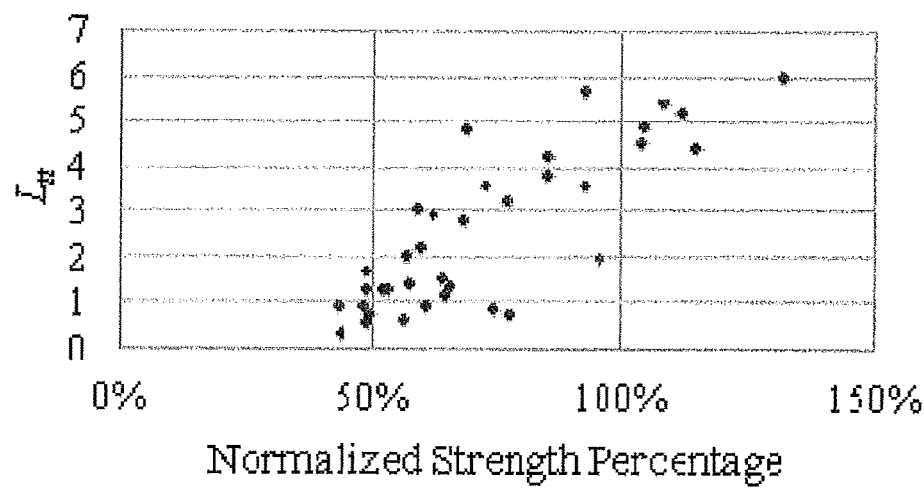
Figure 5C:
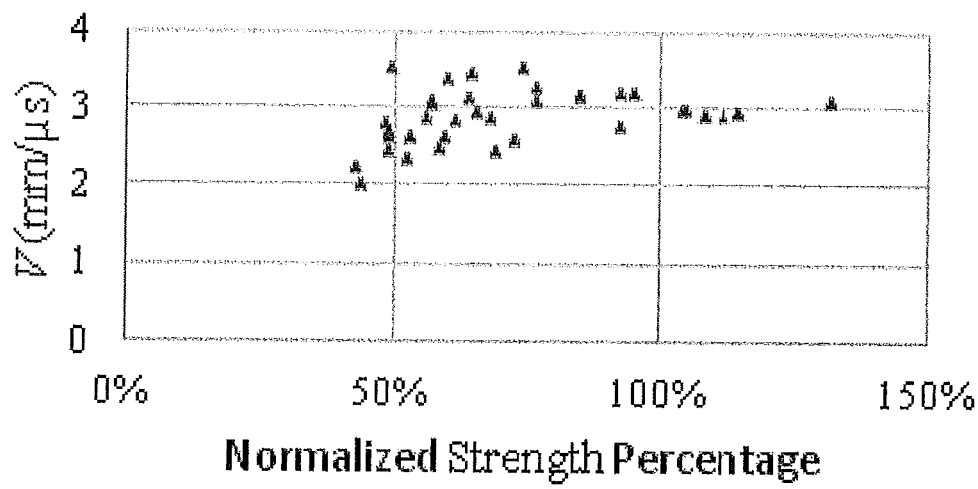
Figure 5D:
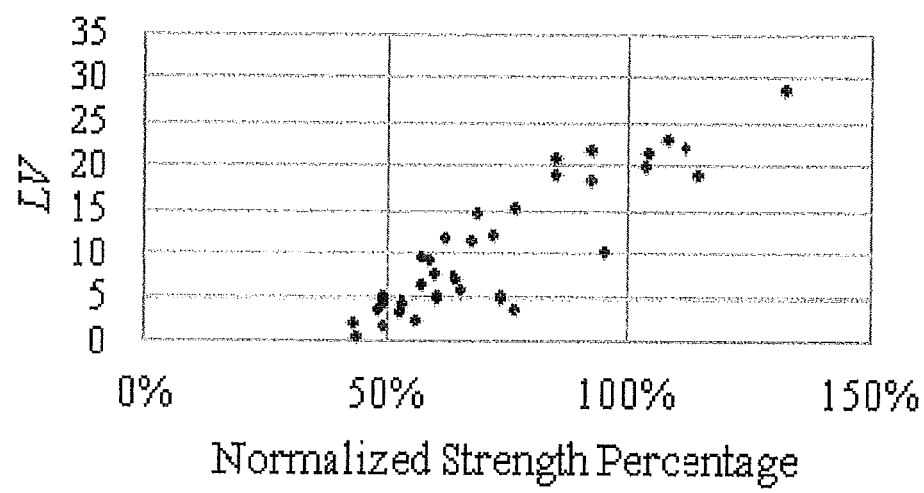
Figure 6:
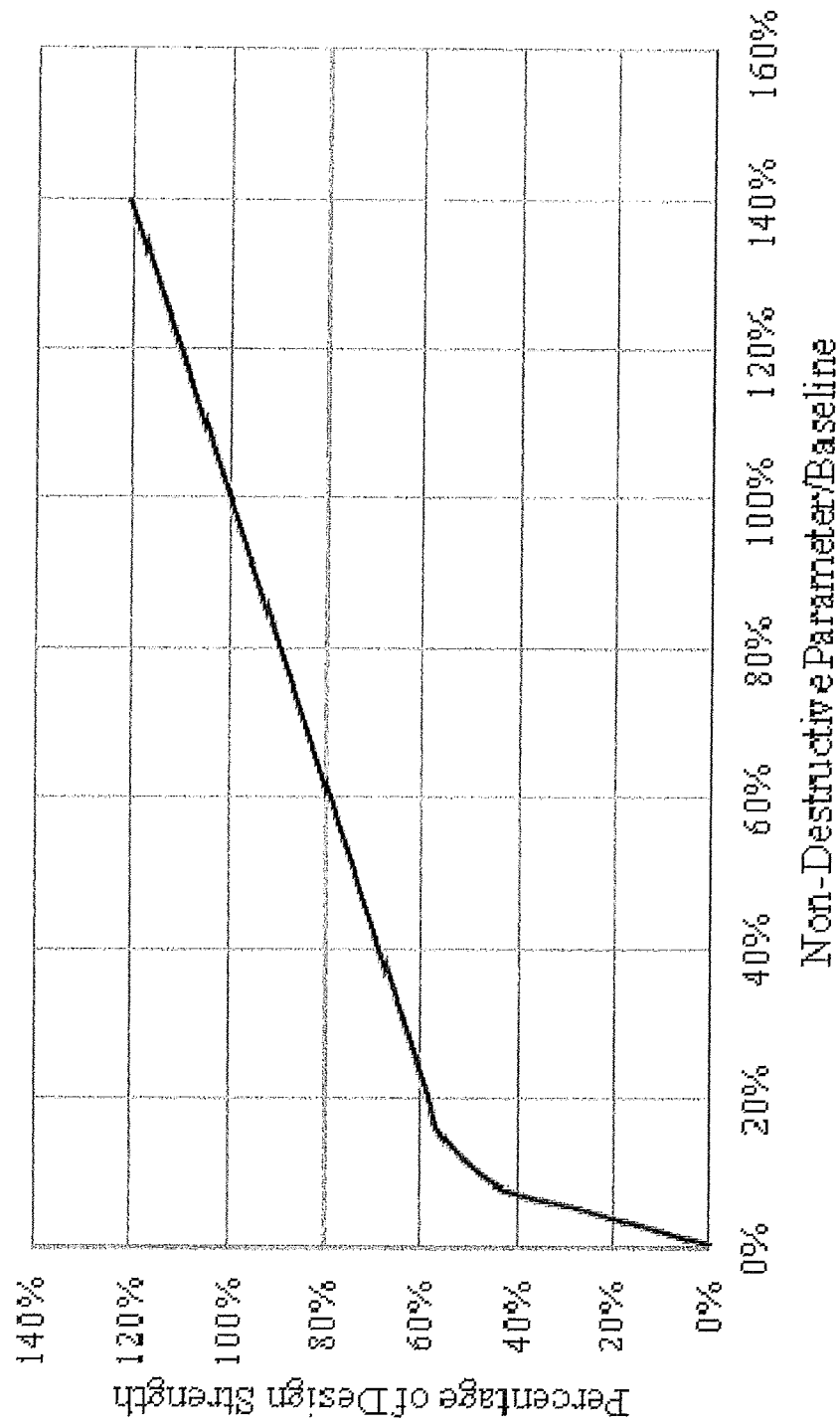
FIG. 6 illustrates a conversion curve.

FIG. 5(c) shows the data where sonic velocity was calculated according to equation (5). The correlation coefficient for this data (Table 2) shows poor correlation with Strength Percentage. As well, correlation between sonic velocity and $L_{tt}$, which does not include knowledge of material thickness, was poor at 0.365. This discussion shows that sonic velocity generally should not be used as an indicator of composite strength in the applications considered here and it cannot be modeled using the ultrasonic parameters discussed here.

From examination of the data in FIG. 5(c), it appears that sonic velocity may converge to a narrower range at higher Strength Percentage. From this, at best, one can only be expected to provide a possible range of thickness.

2.4 Baseline Calculation

The intent of this paper is to identify values that could be used as Baseline, or starting, values for composites being evaluated for mechanical strength. The results described above show that two (2) parameters calculated from ultrasonic readings can be used to determine the strength of a glass reinforced composite as a percentage of the value determined from lamination analysis. From the data that was considered in this paper, solving the linear regression curves for the value that produces 100% will yield the baseline values.

For the two (2) parameters selected above, the Baseline values are shown in Table 3. For composites where the original parameters are unknown, assuming that the original strength was 100% of the calculated value would allow use of these values to determine the starting point. The ratio of current values to the baseline value can be used with the conversion curve shown in FIG. 4 to provide the Strength Percentage.

Note in FIG. 4 that the slope of the curve changes where the percentage of design strength is about 45%. This is done to take the strength percentage to 0% when the parameter is 0. However, at this point, the change in slope is not supported by data, since no samples tested in this paper have Normalized Strength Percentage less than 43%.

TABLE 3

Baseline Values

| Parameter | Baseline Value |
|---|---|
| $L_{tt}$ | 4.2606 |
| LV | 19.085 |

In the case where ultrasonic readings can be taken from a composite before it is put into service, the results of the readings can be used with the baseline values above and FIG. 4 to provide the starting point value for future evaluations.

This disclosure has shown that non-destructive ultrasonic methods can show strong correlation with the bulk elastic modulus of a wide range of fiber reinforced composites. Conventionally, it has been shown that the reduction in bulk modulus appears to occur at the reinforcement-to-matrix interface, inferring that this modulus reduction is independent of the type of fiber reinforcement. Damage of these interfaces has been produced in the laboratory by several means, including absorption of liquids and mechanical stresses—the same conditions that many structural composites must accommodate.

The correlation of parameters determined from the ultrasonic readings has been demonstrated, above. When ultrasonic readings are taken from a reinforced composite and processed by the method described herein, changes in the values of the parameters calculated using equations 4 or 6 are used to determine the current modulus value using FIG. 4.

In practical application, the strain at failure is generally relatively constant for a composite. Reductions in bulk modulus will see the strain increase at a constant stress—therefore showing reduced strength. Thus, as the bulk modulus declines due to various environmental and loading conditions, the strain within the composite will increase. Failure will occur when the strain has increased to the failure level without any change in the load or application conditions.

The ultrasonic methods described herein can be applied to composite structures for the purpose of monitoring changes in the bulk modulus of the material. When the Strength Percentage is determined for an as-built composite—or LV or $L_{tt}$ are determined directly from the as-built structure—then changes in the bulk modulus can be determined from ultrasonic readings. Over time, the changes in bulk modulus can then be incorporated into risk assessment to determine whether the resulting strains are acceptable and to project remaining service life.

This is similar in outcome to thickness testing of metallic structures for the same purpose. In this case, the elastic modulus remains constant but the stress level increases due to reduction in area.

Most composite structures presently in use did not have the new Strength Percentage, LV or $L_{tt}$ determined when they were new. As such, they do not have a known starting point from which to determine the rate of change or to make projections. In these cases, use of the baseline values listed in Table 3 is intended to allow initial risk assessment to be conducted. Because the testing is non-destructive, the risk assessment can be updated frequently with minimal effect on the structure.

A further item to discuss is that the parameters calculated did not require explicit calibration standards. Only the samples provided were used with no outside reference standards. As well, different ultrasonic equipment—flaw detectors and transducers—were used for some of the samples. This makes it possible to use ultrasonic methods for strength evaluation of existing composite structures without access to calibration standards.

The experimentation has been conducted on a wide variety of composites made using open-mold methods with epoxy vinyl ester matrices and glass reinforcements. Similar results have been achieved with other constituent materials and construction methods, as well as with other manufacturing and exposure effects.

The following conclusions are expected based on the foregoing:

Ultrasonic readings can provide reliable information about the current strength of reinforced polymers;

Changes in composite strength determined using ultrasonic methods can be used for life prediction;

Composite strength values can be provided without using calibration standards;

Sonic velocity does not provide reliable correlation with composite strength; and The calculation methods used in can generally be applied to at least open-mold composites.

A further experiment was conducted on new glass reinforced thermoset, which were obtained from various sources. The specimens were of varying sizes and compositions. Testing was completed on 46 specimens with an average of 39 readings per specimen. All readings were taken without overlap. Forty-one (41) of the specimens were composed only of glass fiber reinforcement in a polyester or vinyl ester matrix. Five of the specimens included various amounts of sand filler.

The readings were taken using Olympus Epoch 1000 ultrasonic flaw detector with M2008, 0.5 MHz transducer.

3.1 Hypothesis

The hypothesis of this work is that quantitative non-destructive parameters can be obtained from new glass reinforced composites to demonstrate consistent properties.

3.2 Ultrasonic Testing Background

In this experiment, an ultrasonic transducer was used to apply a short, small displacement pulse to the surface of the composite. The pulse time was approximately 1 microsecond, corresponding to a frequency of 0.5 megahertz.

The pulse transits the material though the thickness until it reflects from the free opposite surface and returns to the origin. Along the path, the energy of the pulse is attenuated by the material and various features within the composite. Between pulse applications, the transducer is used to receive the reflected signals. The reflected signals are then accumulated according to the time after the pulse was applied.

Figure 7:
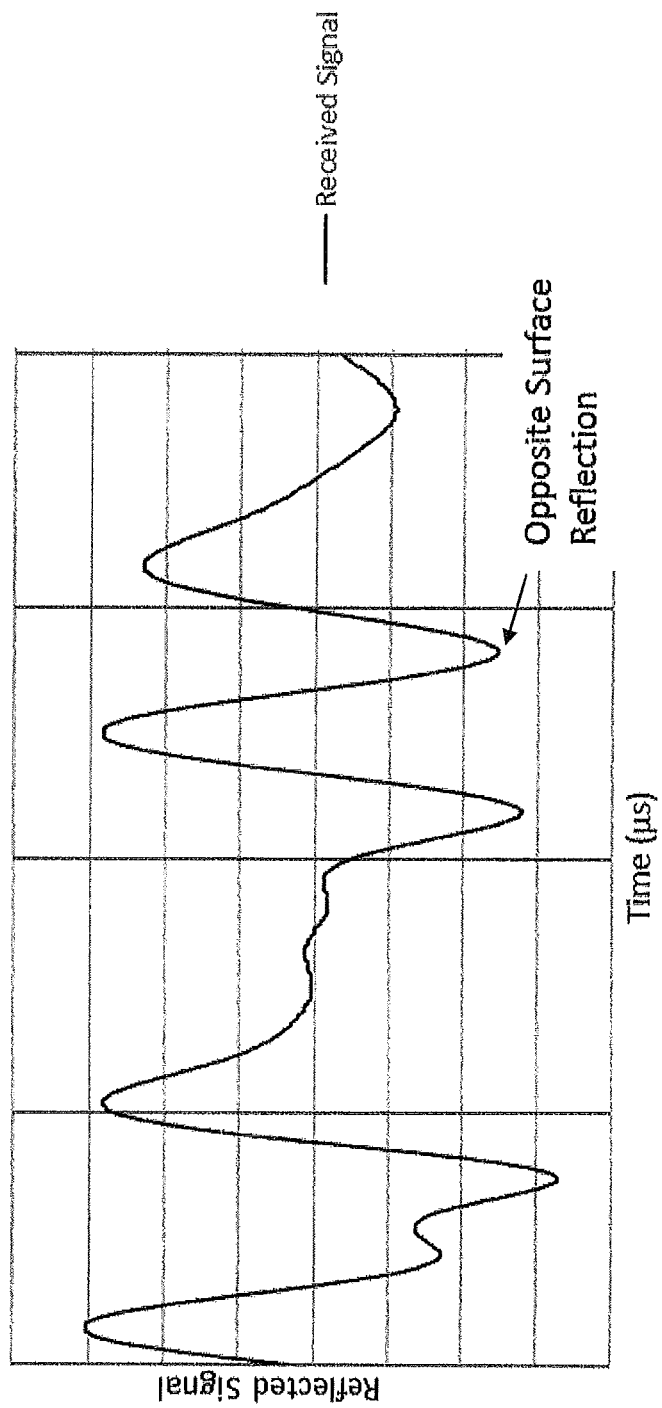
FIG. 7 illustrates an example A-scan.

The output available from the ultrasonic equipment are displayed on an x-y display, with time along the horizontal axis and the averaged magnitude of the received signal displayed vertically. This output is referred to as an "A-scan". An example is shown in FIG. 7, where the signal reflected from the opposite surface is labeled.

3.3 Sonic Velocity

The study that was completed was to take ultrasonic readings from one surface of the specimen, spaced adjacent to each other. The thickness of the specimens was known. From each reading, the transit time for the applied signal to return from the opposite surface of the material was determined and the sonic velocity (V) was calculated according to equation 5.

$$V = 2 \times \frac{\text{thickness}}{\text{transit time}} \quad (5)$$

3.4 Flexural Modulus Variation

Flexural modulus of a composite laminate is not usually considered as a fundamental parameter of the material. It does, however, relate to how well the layers are bonded to each other and the reinforcement is bonded to the resin. These properties are generally of importance to industrial users, especially for fluid containment and support of bending moments.

Figure 8:
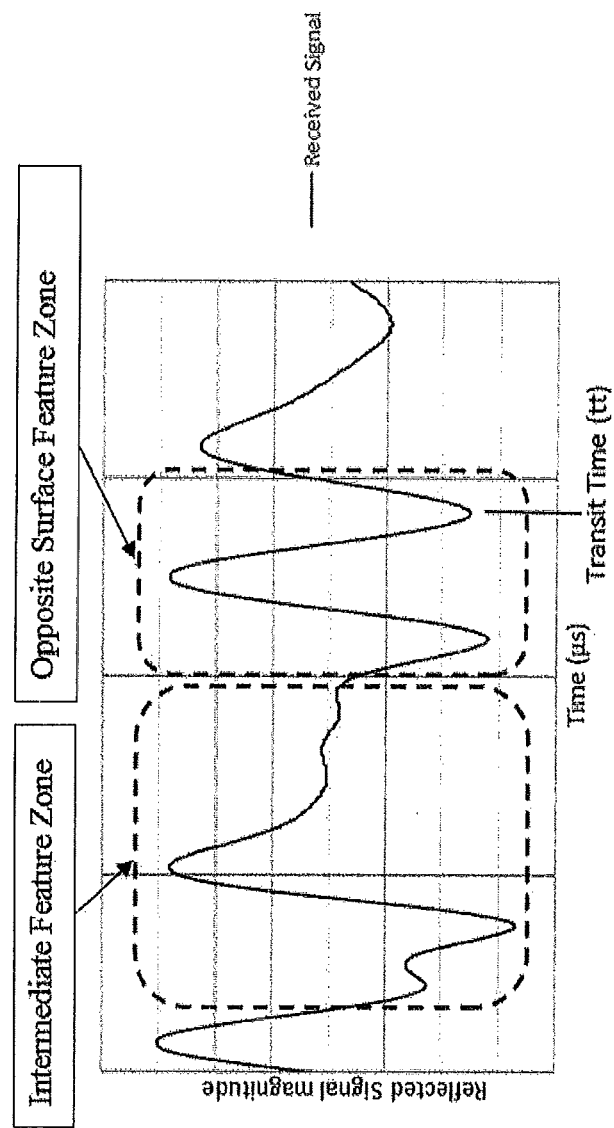
FIG. 8 illustrates data extraction from the A-Scan of FIG. 7.

FIG. 8 illustrates two feature zones within the A-Scan from FIG. 7. From the Opposite Surface Feature Zone, the x-y plot data is used to calculate the overall reflected ultrasound from the full structural thickness of the composite. The x-y plot data from the Intermediate Feature Zone is processed and the results are incorporated with the opposite surface result to determine a value related to the overall attenuation of the applied signal. The value that is calculated has been given the variable name L and a functional description is given in Equation 2.

$$L = f(\text{attenuation}) \quad (2)$$

Calculation of L may be determined by the analysis module 125 by processing of the raw data from the ultrasonic instrument. After L is determined, it is formed into the parameter $L_{tt}$, according to equation 4. The $L_{tt}$ may be determined using data directly from the ultrasonic readings and is intended not to require any additional calibrations or measurements.

$$L_{tt} = L \times \text{transit time} \quad (4)$$

The $L_{tt}$ may be determined from the A-Scan of each reading recorded. For each specimen, the average value was calculated and the differences between the individual values and the average were determined. The distribution of the differences was evaluated.

4.1 Sonic Velocity Results

Figure 9:
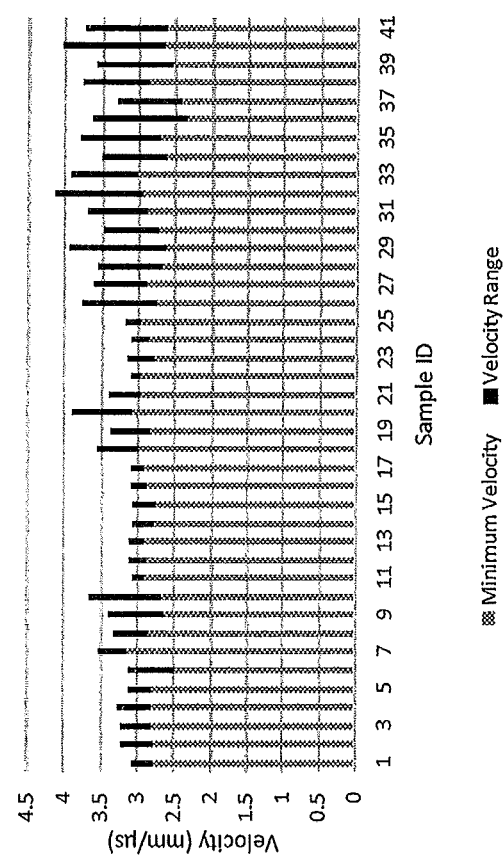
FIG. 9 illustrates velocity for samples that do not contain sand filler.

The sonic velocity distribution among the samples that did not contain sand filler is shown in FIG. 9. Note that for each sample, there is a fairly narrow range of velocity values calculated. There are some similarities in the data.

Figure 10:
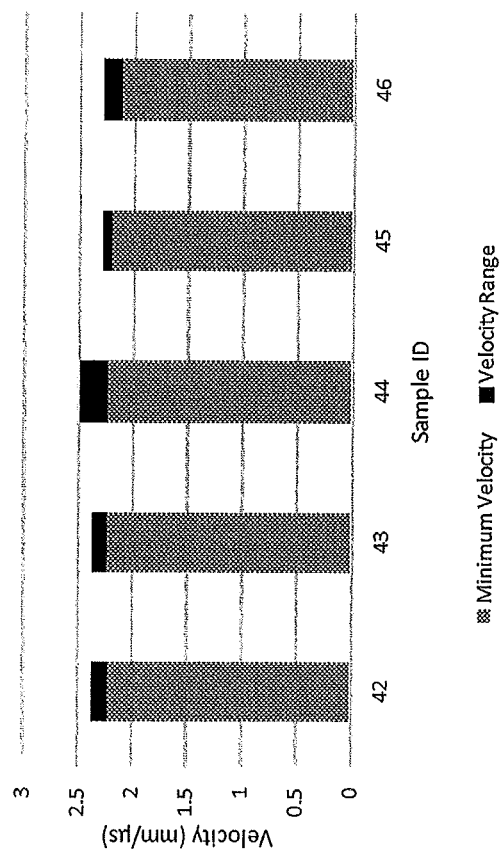
FIG. 10 illustrates velocity for samples that do contain sand filler.

The sonic velocity results for the specimens with sand filler are shown in FIG. 10. Note that the velocity values for this case are lower than in FIG. 9. For the samples shown, the mean is 2.29 mm/µs and the standard deviation is 0.047 mm/µs.

Figure 11:
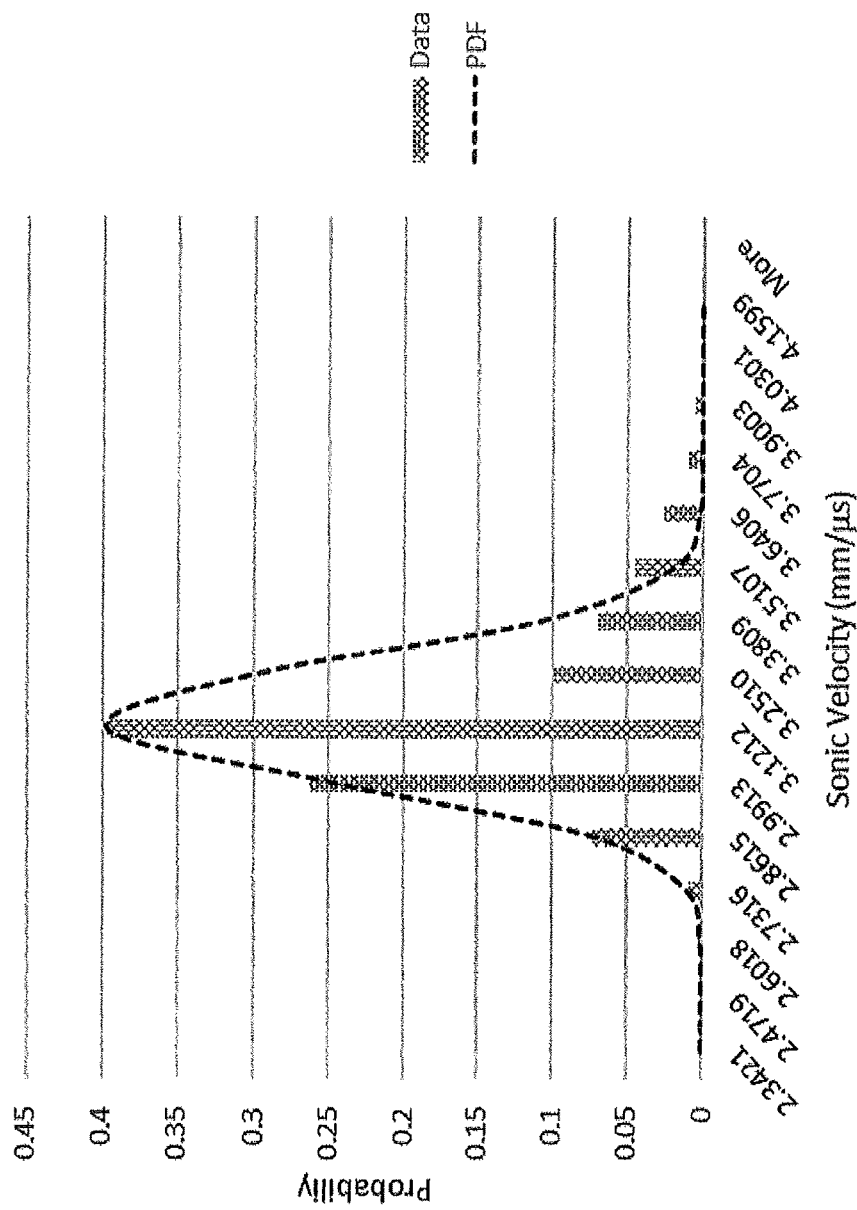
FIG. 11 illustrates the velocity data and normal distribution for samples not containing sand.

FIG. 11 illustrates a histogram of all sonic velocity values for the samples with no sand fill lumped together with an imposed normal curve with a mean of 3.14 mm/µs and standard deviation of 0.149 mm/µs. When the calculated probabilities are compared to the histogram fractions they are from the same population to a significance of 82%. A similar curve with different mean and standard deviation for the sand-filled specimens yields ANOVA significance of 81%.

For most new composites, the thickness is generally expected to be within a fairly narrow range, so ultrasonic readings should be expected to give a narrow range of transit time values as calculated using the velocity range shown in FIG. 11. In FIG. 11, the 95% confidence interval of sonic velocity corresponds to ±9.3% of the mean. This means that FRC with constant thickness will yield ultrasonic transit times with a corresponding confidence interval.

An appropriate quality specification for FRC would be to require that the confidence interval for transit time be within the confidence interval identified above and factored by the allowable thickness range. Unseen fillers and porosity are expected to reduce the sonic velocity which would be directly observable from transit time results. From this, unseen defects in a FRC laminate can be detected. Sonic velocity of FRC has been observed to decline from some service conditions. After the sonic velocity is determined for a new sample, a quality parameter can be reported with the knowledge that the quality parameter may provide guidance for future inspections.

4.2 $L_{tt}$ Variation

Figure 12:
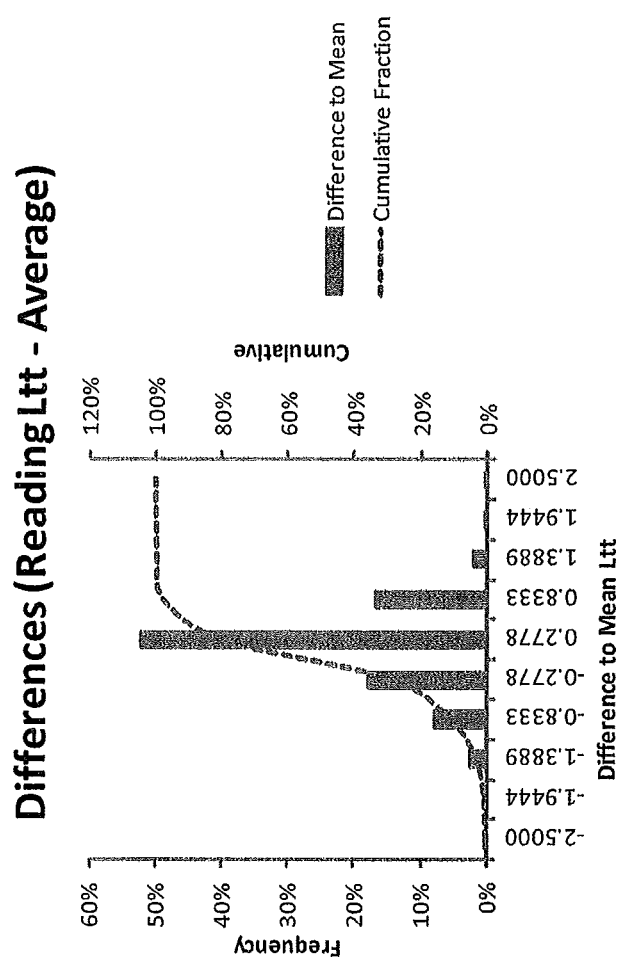
FIG. 12 is a histogram illustrating the difference to mean $L_{tt}$.

As discussed above the variation of $L_{tt}$ values calculated for each reading was determined. FIG. 12 is a histogram of distribution of the differences and the cumulative fraction. From the histogram, it may be noted that there is variation from the mean in almost all readings. The results illustrate that the variation from the mean is confined to a narrow band. The actual data was found to conform well to a normal distribution with mean of 0 and standard deviation of 0.42, making the 95% confidence limits ±0.81 with a nominal average $L_{tt}$ of 3.50.

The average $L_{tt}$ value from a new composite will also serve as a starting point to allow the progression of damage to be measured and evaluated while the FRC component is in service. It has been shown that the value of $L_{tt}$ correlates directly to the flexural modulus of FRC—thereby indicating changes in the inter-layer and fiber-matrix bonding. A close correlation of $L_{tt}$ to tensile modulus has also been shown.

A small value for standard deviation of $L_{tt}$ is expected to relate to lower variation in the FRC and therefore more consistency in properties. An appropriate quality specification would be to require that 95% of all $L_{tt}$ values for a new FRC be within the 95% confidence limits. Through the experiments, it has been determined that in a number of cases that defects in FRC will generally reduce the $L_{tt}$ value to outside of the confidence limits. Thus allowing detection of defects.

$L_{tt}$ of FRC has been observed to decline due to service conditions such as high stress and corrosion. After the $L_{tt}$ is determined for a new sample, the corresponding structural capacity can be determined and this can be used in future inspections to determine structural changes taking place in the FRC. Both velocity and $L_{tt}$ values may be calculated from one ultrasonic reading.

From the experiments, it was determined that 30 ultrasonic readings from FRC that is expected to be constant thickness is expected to produce a valid mean and standard deviation. For 30 readings, adding one reading is expected to make less than 3% difference to the standard deviation from the value determined for 29 readings. Therefore an ultrasonic quality assessment may be completed with approximately 30 readings.

In a further experiment, 56 test specimens were examined. Of these specimens 41 were composed of polyester/vinyl ester resin and glass while 15 also includes various weight percentage of sand. In this experiment, the focus was on two particular parameters, namely the sonic velocity and the flexural parameter.

$$V = 2 \times \frac{\text{thickness}}{\text{transit time}} \quad (5)$$

$$L_{tt} = L \times \text{transit time} \quad (4)$$

Figure 13A:
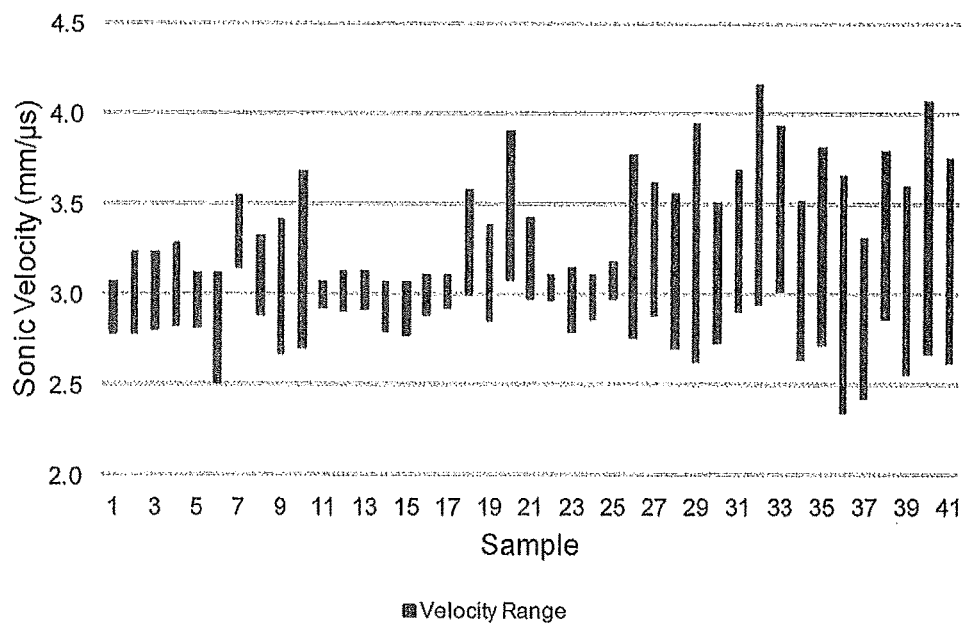
FIGS. 13A and 13B illustrate sonic velocity results in an experiment using an embodiment of the system and method described herein.
Figure 13B:
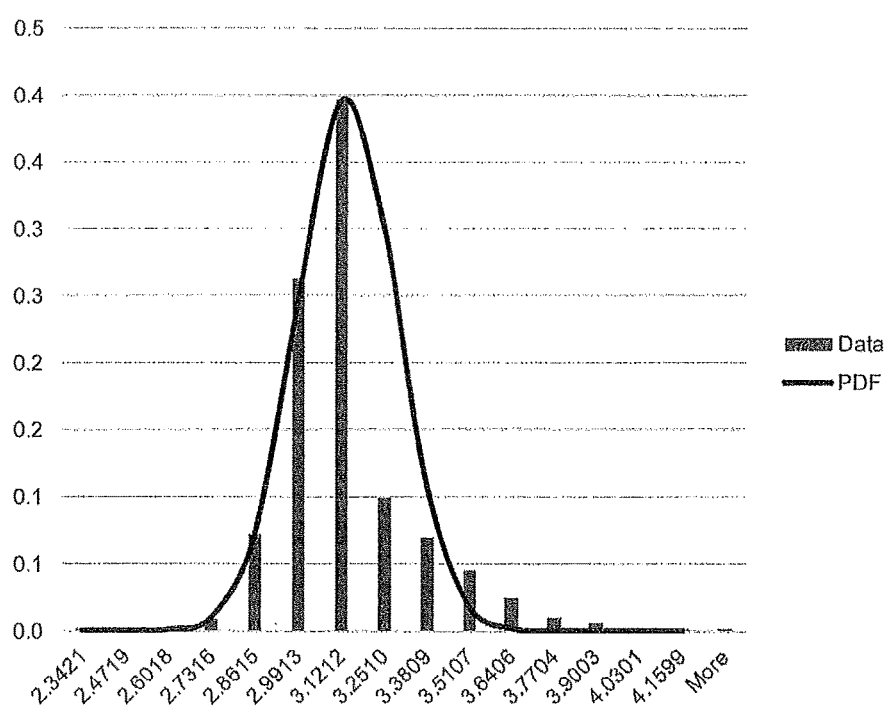

FIGS. 13A and 13B illustrate the sonic velocity with no sand addition and the distribution with no sand. In particular, it can be viewed that there are overlapping ranges of the velocity range and the distribution illustrates a normal to 0.82 significance measure.

Figure 14A:
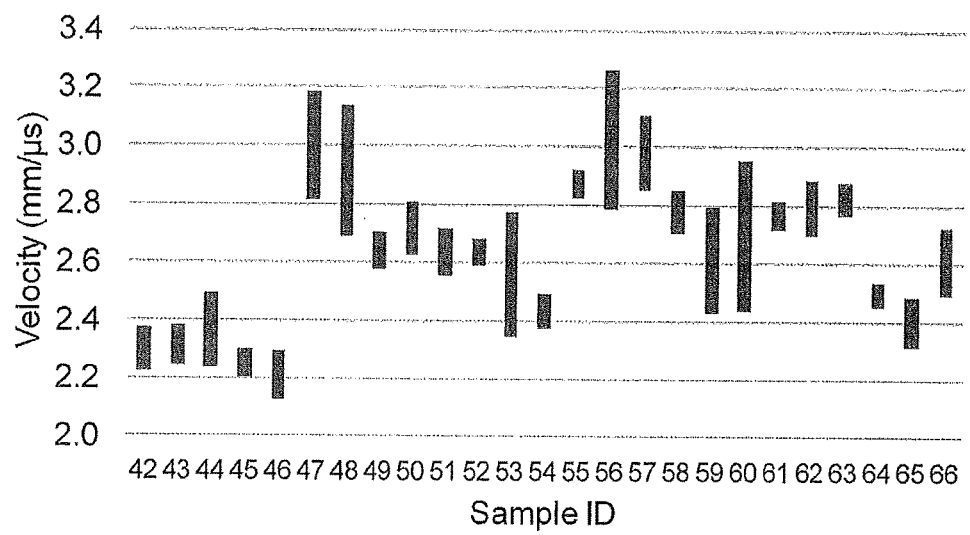
FIGS. 14A and 14B illustrate sonic velocity results of polymers including sand in an experiment using an embodiment of the system and method described herein.
Figure 14B:
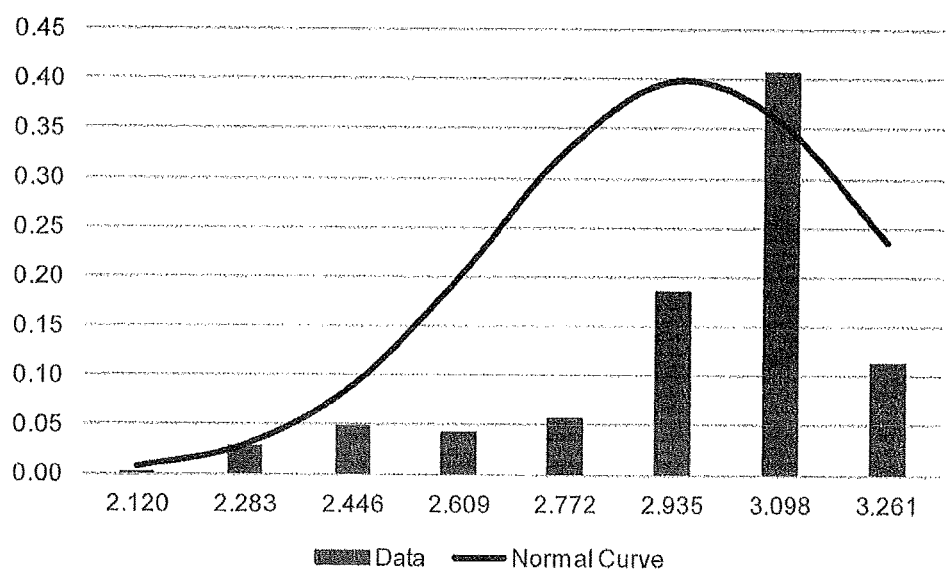

FIGS. 14A and 14B illustrate the sonic velocity with the sand included in the matrix. From FIG. 14A, it can be seen that there is a wide variation between the samples. The distribution shown in FIG. 14B also illustrates that the variation from sand is significant and that the distribution is normal to 0.21 significance.

Figure 15A:
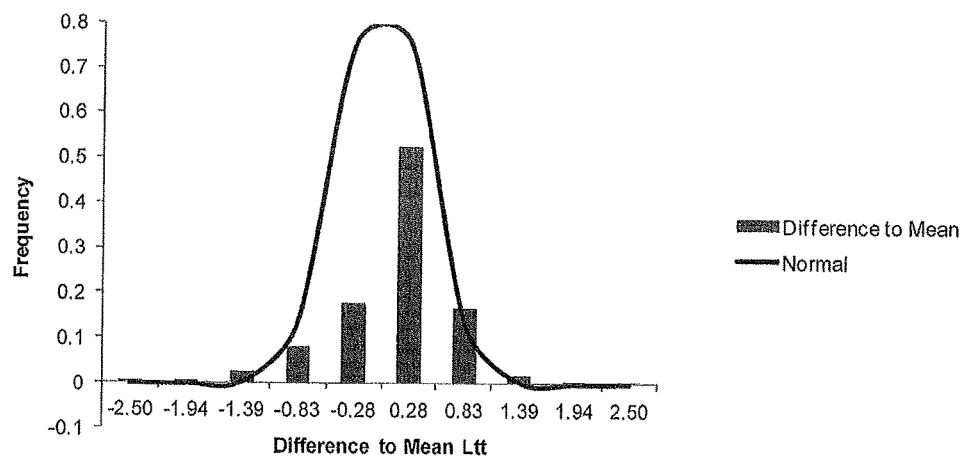
FIGS. 15A and 15B illustrate flexural parameter results in an experiment using an embodiment of the system and method described herein.
Figure 15B:
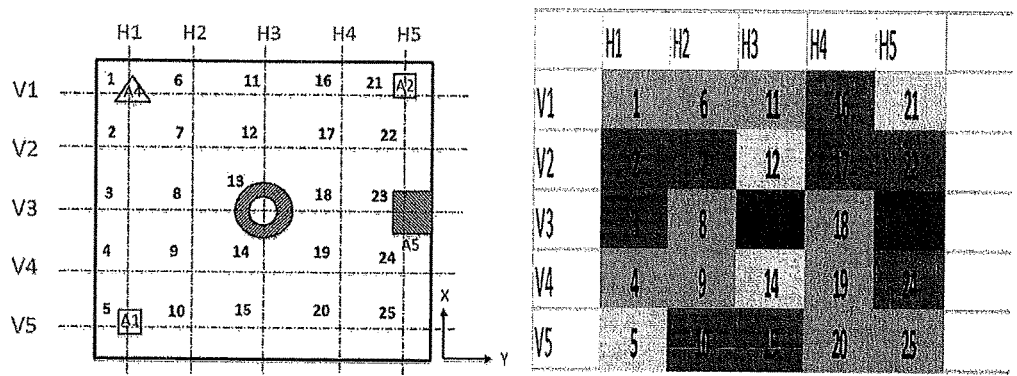

FIGS. 15A and 15B illustrate the flexural parameter results. These results may be calculated after each reading and may use only data from the ultrasonic data as no external information is required. The flexural parameter results are intended to predict local and overall structural properties and pinpoint potential defects. Small differences to the mean indicate consistency. FIG. 9A is a histogram illustrating differences to the mean and illustrates that variations beyond −0.83 may be a defect. FIG. 9B further illustrates defect detection.

A full set of ultrasonic readings to assess FRC of the same thickness can be obtained with approximately 30 or more ultrasonic readings using the method described herein. The sonic velocity of a composite is be expected to be within a narrow range. The transit time for an ultrasonic signal though FRC has been found to be directly proportional to the thickness and sonic velocity. Based on the expected range for sonic velocity as shown above, and the thickness tolerance, the transit time for an ultrasound pulse to transit the material can be specified to be within a known range.

In addition, the existence of defects and fillers in the FRC can be detected from transit time variations that result from sonic velocity variations. $L_{tt}$ variation from the mean should be expected to be within a defined range for the composite which is intended to be less than approximately ±0.82 and should be expected to conform well to a normal distribution with mean of 0 and standard deviation of 0.42. The existence of defects in the FRC may be detected from $L_{tt}$ variations. The existence of significant defects may reduce the calculated $L_{tt}$ value at the defect. The values for sonic velocity and $L_{tt}$ determined for new FRP may be used to determine changes taking place in service conditions.

Figure 16:
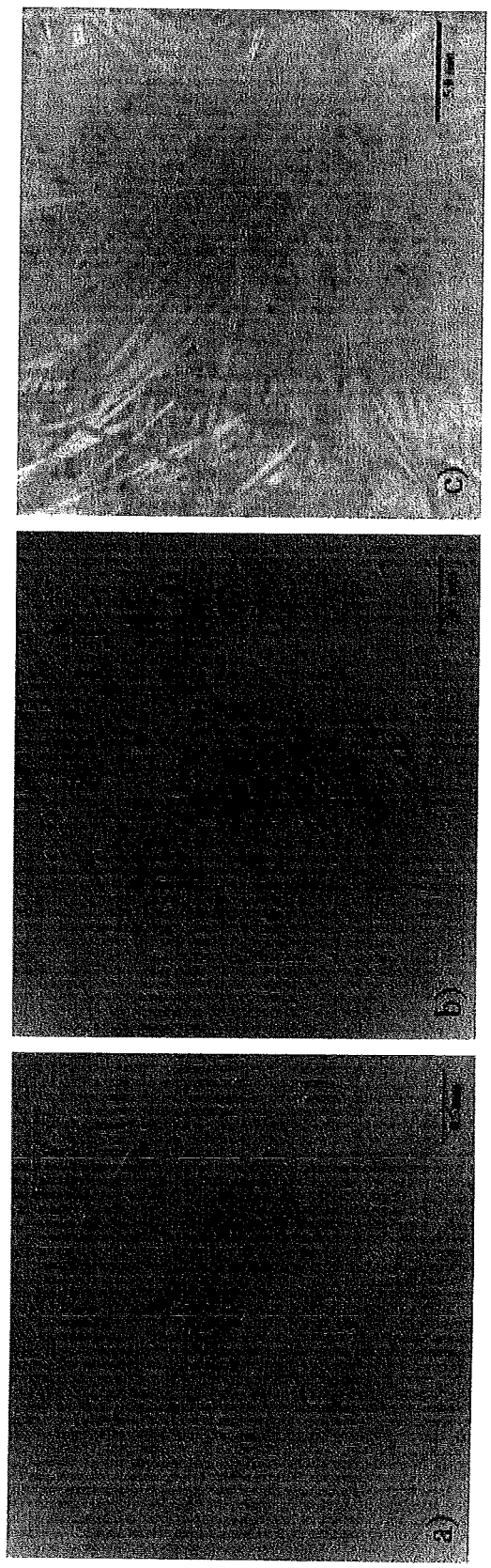
FIG. 16 illustrates stereography images for glass fiber constituents after burn-off, for fibers with an angle of −57°, fibers with an angle of +57°, and fibers with random orientation.

Case studies have also been conducted using the method and system described herein. In a first case study, FRC pipes with 457.2 mm (18") length and diameters ranging from 101.6 mm (4") to 203.2 mm (8") were used. The FRC pipes were manufactured from glass fiber and epoxy vinyl ester using filament winding process. These pipes were fabricated from three distinct layers. The first layer is a liner, a smooth layer with special additives adapted to come into direct contact with the fluid. The main objective of this layer is to provide corrosion and wear resistance for the internal surface of the FRC pipe. The filament layer is the second layer that forms the pipe wall thickness and handles the stresses resulting from the internal and external pressure. Then a final layer of pure resin coating is added to insure smooth surface finish and full fiber impregnation. During the case study, information about the fiber orientation and the fiber weight percentage for the pipes received was not provided. Prior knowledge of the fiber weight fraction, ply thickness, and orientation has been considered to be necessary to obtain reliable ultrasonic testing prediction for the elastic modulus of the FRC pipes. Hence, burn off testing, ply counting and micrographs were performed to obtain this information. Three samples were extracted out the circumferential direction of each pipe and placed in the oven under 500° C. for an hour. The samples were weighed before and after the burn off process and the fiber weight fraction ($W_f$) was calculated using the following relation, $$W_{f(Matrix)} = \left(\frac{m_c - m_f}{m_c}\right) \quad (8)$$

$$W_{f(Fiber)} = 1 - W_{f(Matrix)} \quad (9)$$

where $m_c$ is the total mass of the composite before burn off and $m_f$ is the mass of the remaining constituent after burn off. After burn off the number of the plies was counted and stereomicroscope was used to determine the fiber orientation as shown in FIG. 16. Table 4 shows the burn off and plies counting results.

TABLE 4

FRC pipe burn-off and ply counting results

| Pipe diameter (mm) | Calculated Fiber volume fraction (%) | Average Fiber Weight fraction (%) | Standard Deviation | Number of Plies |
|---|---|---|---|---|
| 101.6 (4") | 34.6 | 50.8 | ±0.8 | 3 ply (57°) |
| | | | | 3 ply (57°) |
| | | | | 4 ply (Random) |
| 152.4 (6") | 40.3 | 56.9 | ±0.4 | 3 ply (57°) |
| | | | | 3 ply (57°) |
| | | | | 4 ply (Random) |
| 203.2 (8") | 39.8 | 56.4 | ±0.7 | 3 ply (57°) |
| | | | | 3 ply (57°) |
| | | | | 4 ply (Random) |

The weight fraction values can be converted to volume fraction using the following relation, $$V_{f(fiber)} = \frac{1}{\left[1 + \frac{\rho_f}{\rho_m}\left(\frac{1}{w_{f(fiber)}} - 1\right)\right]} \quad (10)$$

where $\rho_m$ is the matrix density and $\rho_f$ is the fiber density. The resulted data were used in the theoretical and experimental calculation. The FRC pipes were fabricated from a total of 10 plies. The first 6 plies were stacked in $[-57/+57]_6$ configuration followed by 4 plies of Chopped Strand Mats (CSM) with random orientation. The orientation angle values for the unidirectional laminates obtained experimentally has a difference of 2.5° when compared to the reported value by the manufacturer (i.e. −54.5/+54.5). At orientation angles greater than 45°, a minor change in the orientation angle (i.e. 2.5°) is not expected to have a significant effect on the tensile modulus.

Theoretical Evaluation for Elastic Properties of FRC Pipes

Micro-mechanical model is intended to predict the composite stiffness properties from then properties of its original constituents, listed in Table 5.

TABLE 5

FRC pipe constituent properties

| Material | Density (g/cm³) | Diameter (μm) | Tensile Modulus (GPa) | Tensile Strength (GPa) | Poisson's Ratio |
|---|---|---|---|---|---|
| Glass Fiber (E-glass) | 2.54 | 10 (round) | 72.4 | 3.45 | 0.2 |
| Epoxy Vinyl Ester | 1.3 | — | 3.2 | 0.86 | 0.35 |

The elastic properties for unidirectional continuous fiber can be calculated using the Rule of Mixture (RoM)

$$E_{11} = E_f(1 - V_m) + E_m V_m \quad (11)$$

$$E_{22} = \frac{E_f E_m}{E_f V_m + E_m(1 - V_m)} \quad (12)$$

where $E_f$ is the fiber modulus, $E_m$ is the matrix modulus, $V_m$ is the matrix volume fraction. However, in this study a modified version of the rule of mixture, was used to account for the change in the fiber angle. In order to determine the micro-mechanical properties for the CSM with random orientation, the following equation was used $$E_{CSM} = \tfrac{3}{8}E_{xx} + \tfrac{5}{8}E_{yy} \quad (13)$$

where $E_{xx}$ and $E_{yy}$ are the longitudinal and transverse tensile modulus for chopped unidirectional fibers. In this case the properties are assumed to be the same in all directions in the plane of the lamina (i.e. isotropic).

The elements in the stiffness matrix for an angle ply lamina $[Q_{ij}]$ were determined and then the extensional stiffness matrix and bending stiffness matrix for the laminate was calculated using the Composite Lamination Theory (CLT). For simplicity, the sample assumed to be free from any geometrical curvatures and a perfect interlaminar bond exists between various laminas. The extensional stiffness matrix [A] and the bending matrix [D] were calculated using the following relations, $$A_{ij} = \sum_{j=1}^{N} (\overline{Q}_{ij})(h_j - h_{j-1}) \quad (14)$$

where N is the total number of laminas in the laminate, $\overline{Q}_{ij}$ elements of the stiffness matrix of the $j^{th}$ lamina, and $h_{j-1}$ is the distance from the mid-plane to the top of the $j^{th}$ lamina. The [A] matrix for the FRC pipes can be presented in a matrix form as:

$$[A] = \begin{bmatrix} A_{11} & A_{12} & A_{13} \\ A_{21} & A_{22} & A_{23} \\ A_{31} & A_{32} & A_{33} \end{bmatrix} \quad (15)$$

Table 6 shows the theoretical elastic modulus values obtained using the CLT. It should be noticed that an increase of 4.5% in the calculated theoretical modulus values for the 4" pipe was observed when compared to the value of 8" FRC; this is attributed to the increase of the fabricated FRP pipe wall thickness.

TABLE 6

Calculated theoretical properties of the FRC pipes

| Pipe Diameter (mm) | Total Thickness (mm) | Tensile Modulus (GPa) | Shear Modulus (GPa) |
|---|---|---|---|
| 101.6 (4") | 5.18 | 8.04 | 4.43 |
| 152.4 (6") | 6.04 | 8.24 | 5.07 |
| 203.2 (8") | 7.09 | 8.42 | 5.72 |

In order to obtain a systemic process for measuring and distinguishing the data for each of the given points, a template of a grid system was developed and applied to the provided pipes. The grid system consists of the x-axis (identified by numbers) and y-axis (identified by alphabets) with the origin at the top right. 38.1 mm (1.5") distance between the grid points in both of the circumferential and the longitudinal direction was adapted. Different pipe diameters will result in additional data points of scan in the circumferential direction (i.e. hoop direction) of the pipe. A total of 120, 168 and 228 point were scanned for pipe diameters of 101.6 mm (4"), 152.4 mm (6") and 203.2 mm (8") respectively. Pulse-echo ultrasonic system was used to scan the FRC pipes across the pipe hoop direction. Low frequency flat transducer, 0.5 MHz, with an element diameter of 32 mm (1") coupled with a zero degree vulcanized rubber delay line were used. Readings were taken by holding the transducer in place on the pipe surface and then saving the reading into the memory component of the ultrasonic system. After all readings were taken, the raw reading data was extracted from the instrument. The ultrasonic data was then processed and analyzed by the system described herein which calculates the ratio of expected actual modulus to the theoretical modulus from CLT calculations. The ratio is known as the Percentage of Design Strength (PDS). Mathematically, PDS is expressed as $$PDS = \frac{\text{Actual Tensile Modulus}}{\text{Theoretical Tensile Modulus}} \quad (16)$$

Figure 17:
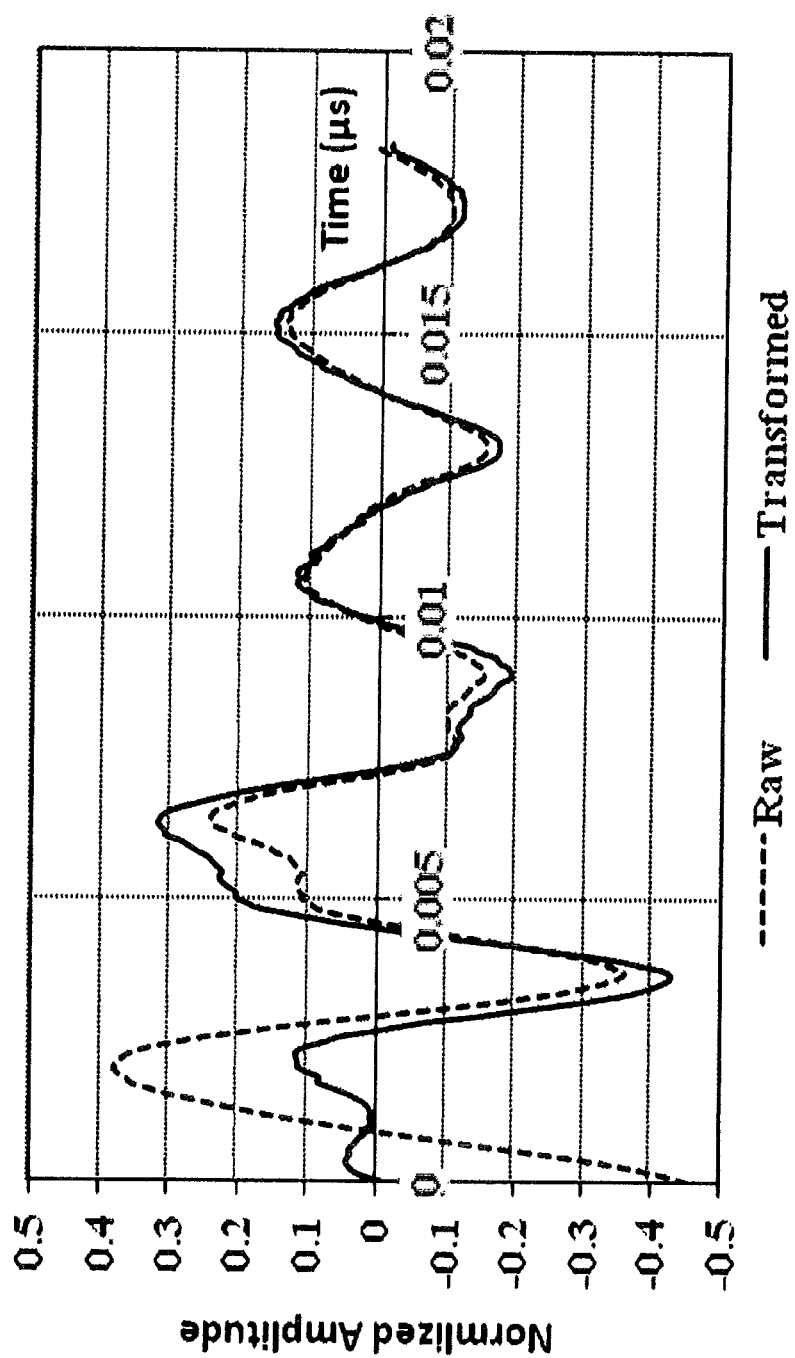
FIG. 17 illustrates raw and transformed reading from a case study detailed herein.

The ultrasonic testing readings that were taken in the scans of the pipes were combined with pipe ID location, and assembled into a data file that could be processed remotely. The raw data was scaled, normalized and filtered to account for variables in the collection process such as transducer characteristics, pipe geometry and surface conditions and environmental conditions. The original A-scan was transformed to allow quantitative analysis. An example of this transformation is shown in FIG. 17. After transformation, pattern recognition was conducted to extract data from the signal reflections from the opposite surface, interfaces or defects within the laminate. The shape of various reflections and the time of their occurrence were analyzed and were used to calculate the shapes and relative magnitudes parameters of the identified signal that were used to determine an attenuation function (L). This attenuation function describes the distribution and magnitude of the losses from the applied signal over the signal path. The PDS was determined from L and the transit time or FRP thickness for the signal across the full pipe thickness. Table 7 summarizes the results of the ultrasonic testing calculations.

Figure 18:
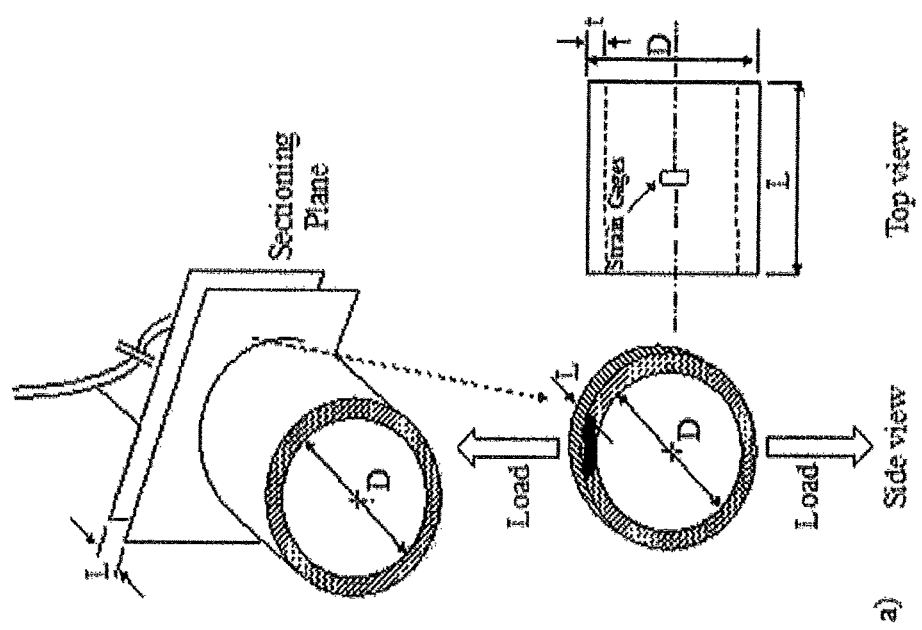
FIG. 18 illustrates an FRC split ring testing scematic.
Figure 19A:
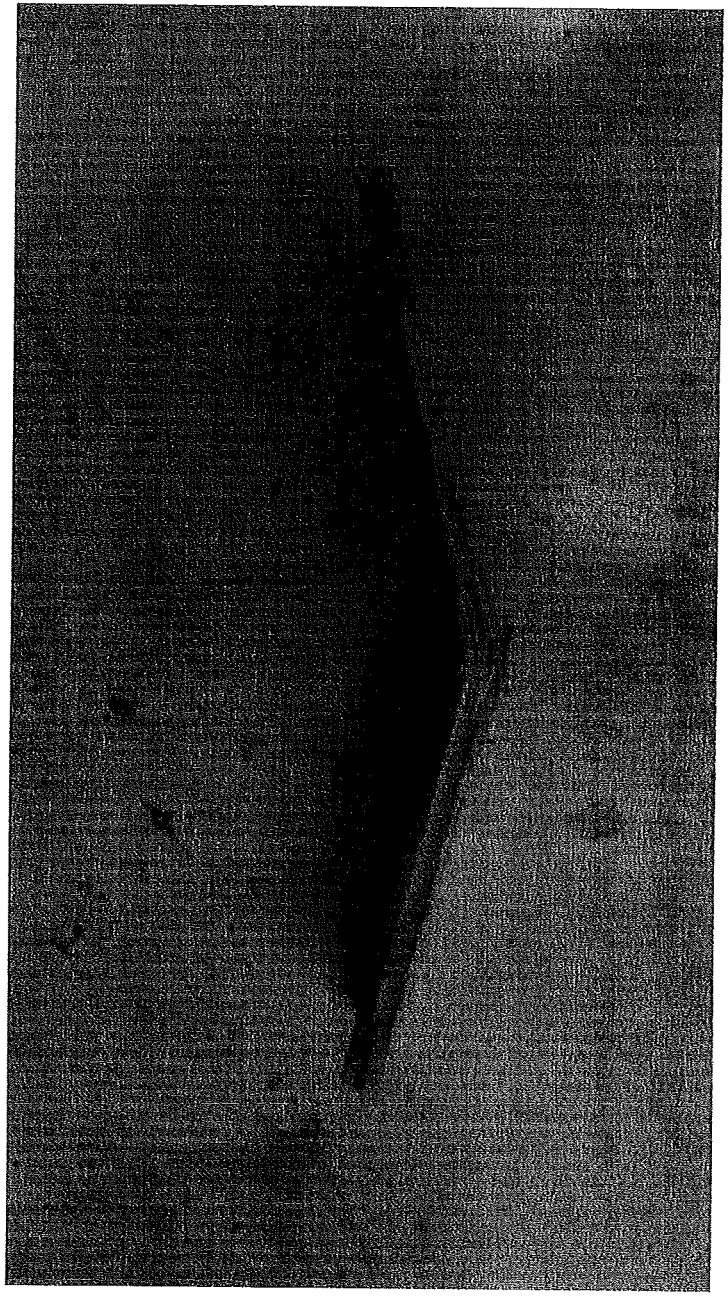
FIGS. 19A and 19B illustrate a sample after fracture and a load deflection curve of the sample.
Figure 19B:
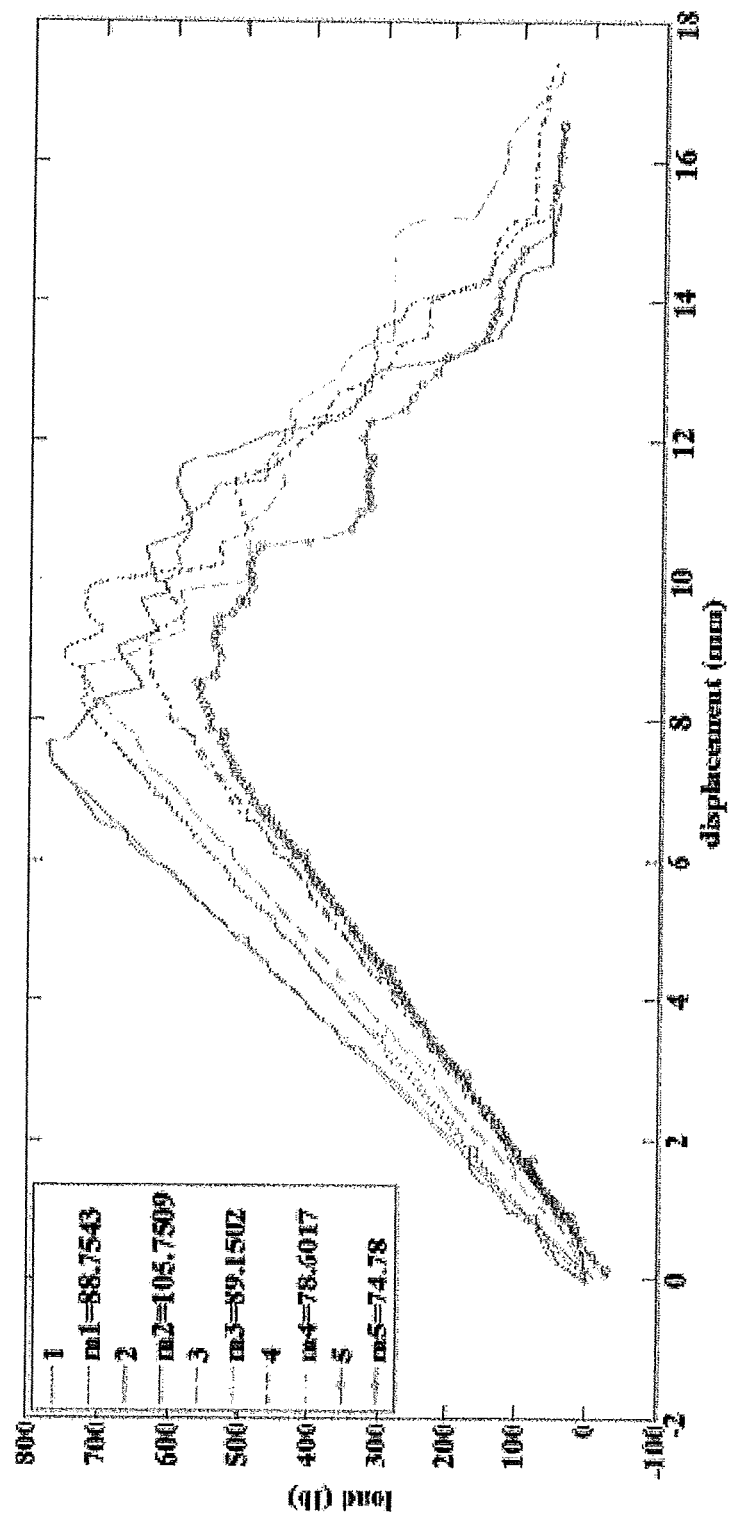
Figure 20A:
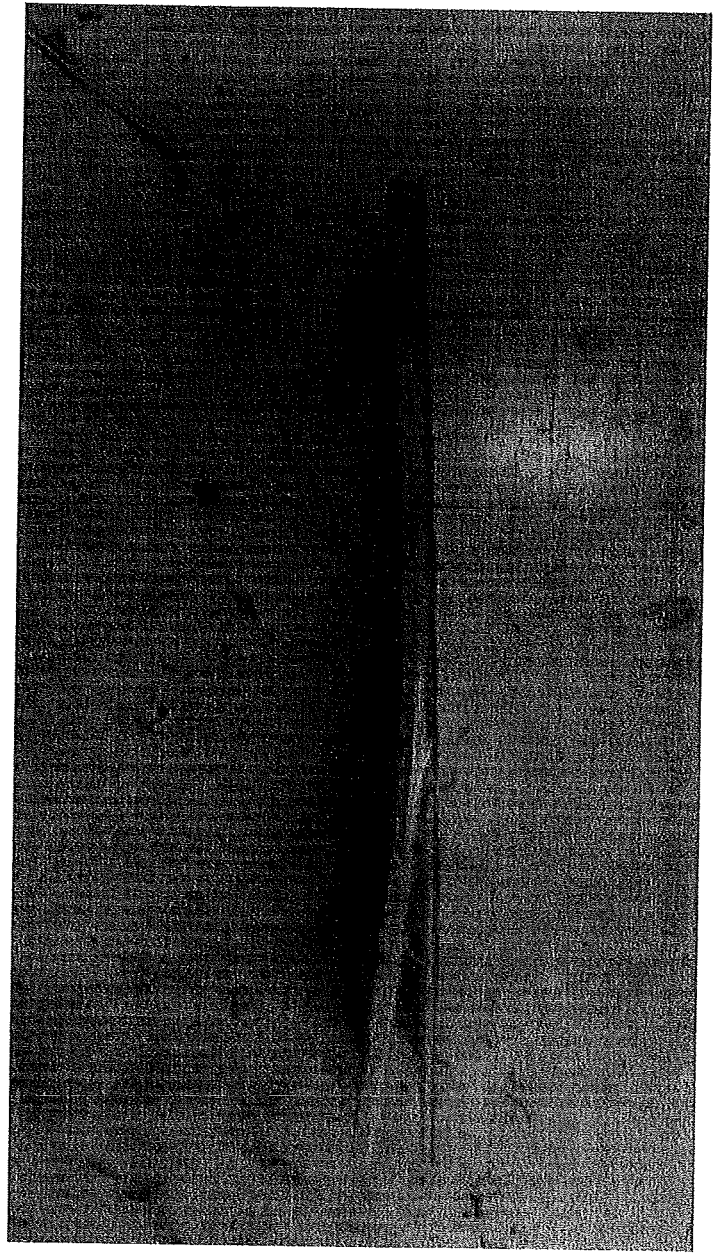
FIGS. 20A and 20B illustrate a sample after fracture and a load deflection curve of the sample.
Figure 20B:
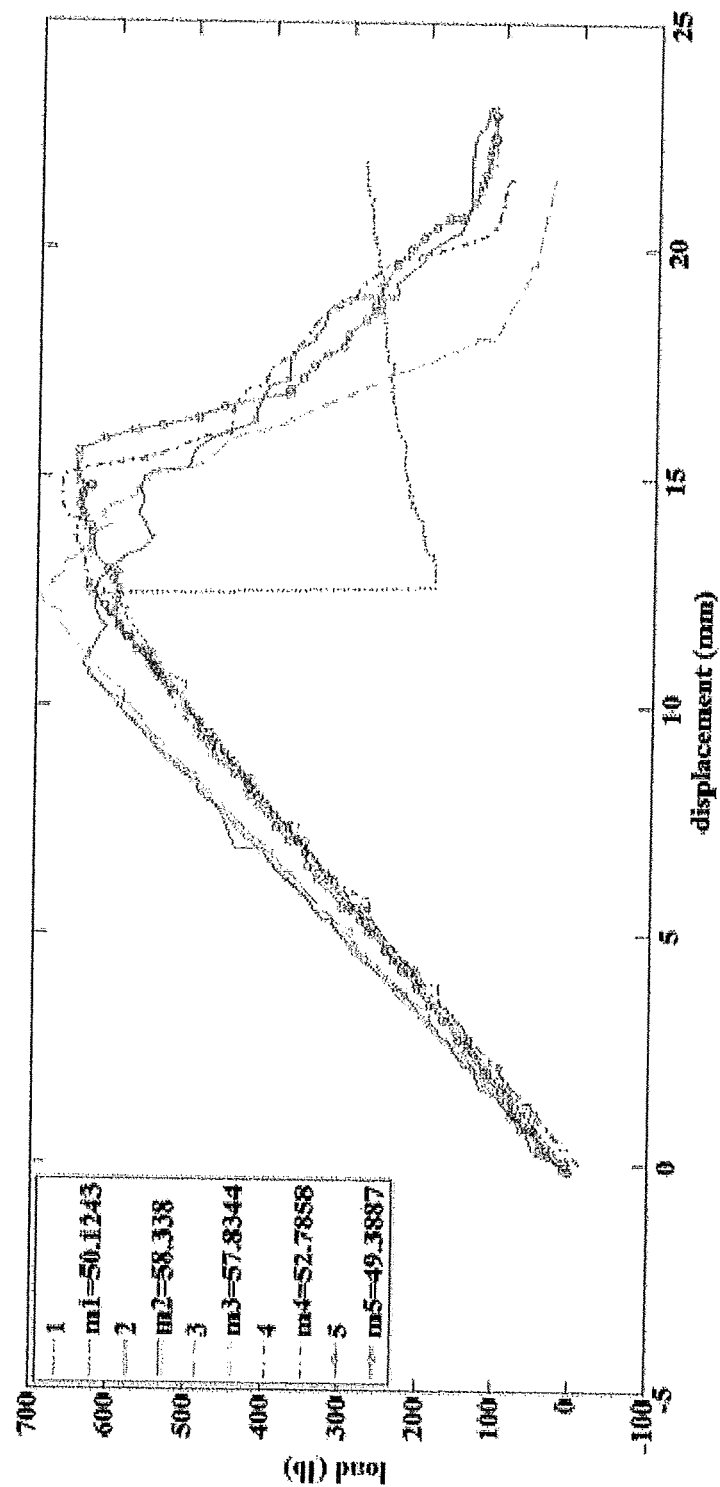

A split ring test was conducted to determine the hoop modulus using (MTS-222 kN) hydraulic testing frame following test standard ASTM D2290, as shown in FIG. 19. In this test the FRC pipe was sliced to sections with a width of approximately 38 mm (1.5") and then mounted on a universal tensile machine using a special testing fixture. The rings were subjected to loading and unloading cycle at a constant loading rate of 3 mm/min. Strain gages were mounted on the FRC pipes outer diameter along the hoop direction, as shown in FIG. 18, to determine the corresponding strain. The maximum load was kept below the yield strength of the composite and the modulus was calculated from the linear regression analysis of the stress strain curve. An average of three rings per each pipe diameter were reported. All pipe rings were tested under elastic deformation and no permanent deflection was applied to the samples. Table 8 show the split ring testing values for two different FRC pipes with diameter of 6" and 8". The average values for three different rings for each FRC pipe diameter were reported. It can be noted from Table 8 that the ultrasonic analysis method described herein has the ability to predict the Hoop modulus accurately. Only a difference of 7.3% and 6.6% in the predicted modulus value was observed when compared to the experimental value obtained by the split ring testing for FRP pipes with 6" and 8" diameter respectively.

TABLE 8

Comparison of Hoop tensile modules obtained by split ring testing and Hoop tensile modules obtained by non-destructive testing

| Pipe diameter (mm) | Spit Ring Hoop Tensile Modulus (GPa) | Predicted Hoop Tensile Modulus (GPa) |
|---|---|---|
| 152.4 (6") | 5.15 ± 0.65 | 4.77 ± 0.41 |
| 203.2 (8") | 7.3 ± 0.46 | 6.82 ± 1.26 |

TABLE 7

Developed ultrasonic method results summary

| | PDS Calculated Using Signal Transit Time | | | PDS Calculated Using FRP Thickness | | |
|---|---|---|---|---|---|---|
| Pipe Diameter | Average (%) | Standard Deviation (%) | Predicted Hoop Modulus (GPa) | Average (%) | Standard Deviation (%) | Predicted Hoop Modulus (GPa) |
| 101.6 (4") | 76 | ±13 | 6.11 | 79 | ±14 | 6.35 |
| 152.4 (6") | 58 | ±5 | 4.77 | 60 | ±6 | 4.94 |
| 203.2 (8") | 81 | ±15 | 6.82 | 86 | ±16 | 7.24 |

The PDS values can be applied to the theoretical modulus values from equation (16) to determine the actual modulus. It was noticed that the predicted modulus values obtained by the method described herein was lower than the theoretical calculated values (i.e. 19% differences for the 8" diameter) FRC. The theoretical calculation for the elastic properties in Table 6 is based on the assumption that there is a perfect bonding between the composite constituents and the material is defect and void free. However, the ultrasonic testing predictions in Table 7 account for discontinuities in materials, voids and the local variation in fiber-matrix bonding. Table 7 shows the corrected values for the ultrasonic testing predicted modulus using the FRC pipe thickness, in practice this correction criteria may be estimated as it may not be possible to determine accurately. In order to measure the actual pipe thickness, both side of the pipe should be accessible, which may not be the case during field inspection.

A further case study was performed wherein two experiments were conducted in parallel to determine the effectiveness of this technology. In the first, ultrasonic readings were taken from the sample and then a 3 point destructive test as per ASTM D790 was performed. In the second, the sample was initially preloaded and then ultrasonic readings were taken followed by the ASTM D790 destructive test. The ultrasonic readings were taken from an embodiment of the system described herein then analyzed by the method described herein.

Samples were separated into two parts each labeled A and B respectively. The following procedure was applied to both samples with the second experiment having an additional step of preloading before any ultrasonic measurements are captured. The preload was applied until the deflection of the specimen reached 3% of the span.

1. Each of these parts was then further separated into 5 specimens with a width of 33 +1/−1 mm and a length which is equivalent to 16 times the thickness of the sample (as per ASTM D790 specification).
2. A 25 mm by 40 mm section was cut from the sample which was used for ignition loss testing to determine the theoretical modulus of the sample.
3. Ultrasonic readings are taken at 32 mm intervals across the entire length of the specimen
4. ASTM D790 destructive tests were performed on each specimen The ultrasonic readings were analyzed and compared with the results obtained from the ASTM D790 destructive tests. The raw data from the ASTM D790 test gives the load-deflection curve of the sample as well as the samples after fracture is shown in FIGS. 19A and 19B and FIGS. 20A and 20B. The modulus from the destructive tests is then calculated as follows:

$$E_B = \frac{L^3 m}{4bd^3} \quad [17]$$

where $E_B$ is the modulus of elasticity, L,m,b and d are the length of the span, slope of the tangent to the initial straight-line portion of the load deflection curve, width of the beam and depth of the beam respectively.

Figure 21A:
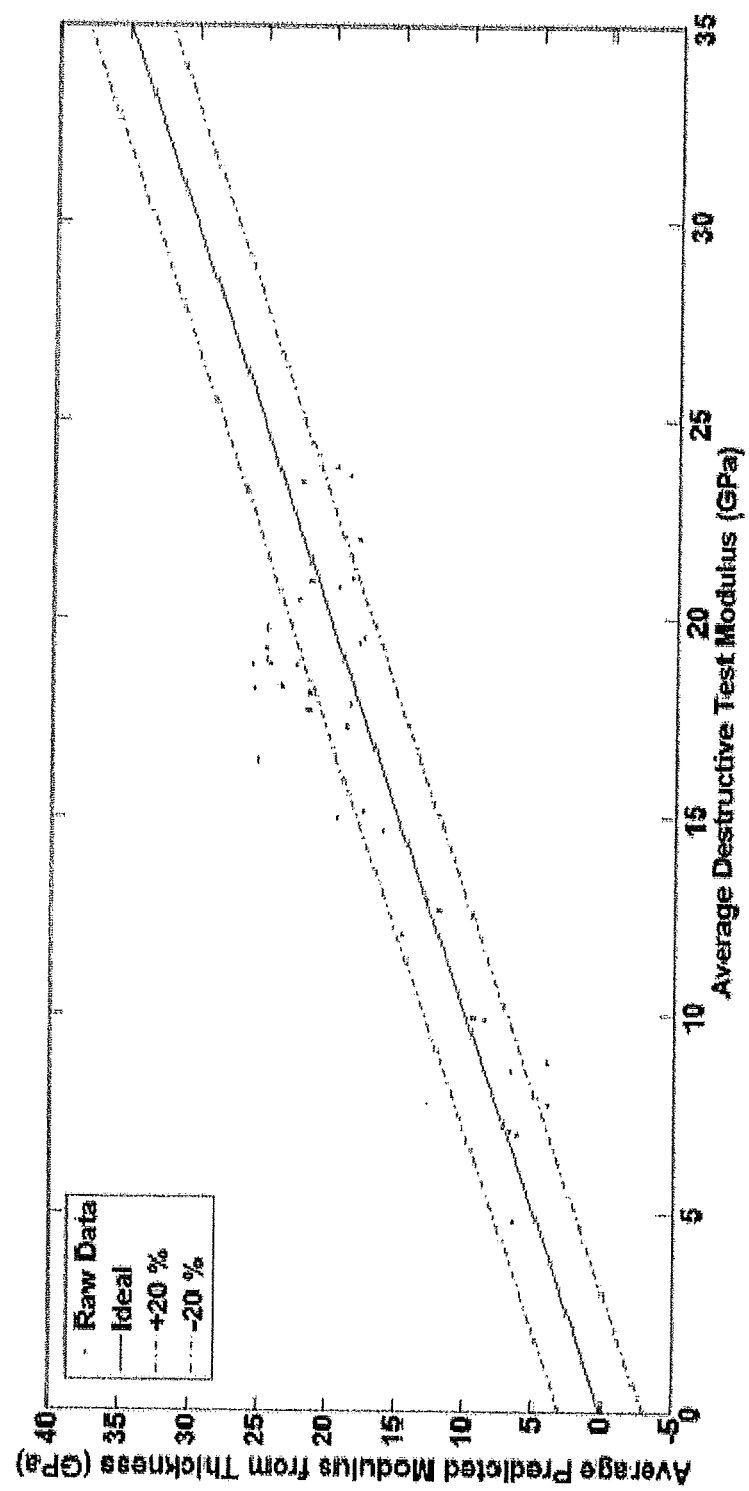
FIGS. 21A and 21B illustrate a comparison between average destructive test modules and predicted modules from thickness (FIG. 21A) and transit time (FIG. 21B).
Figure 21B:
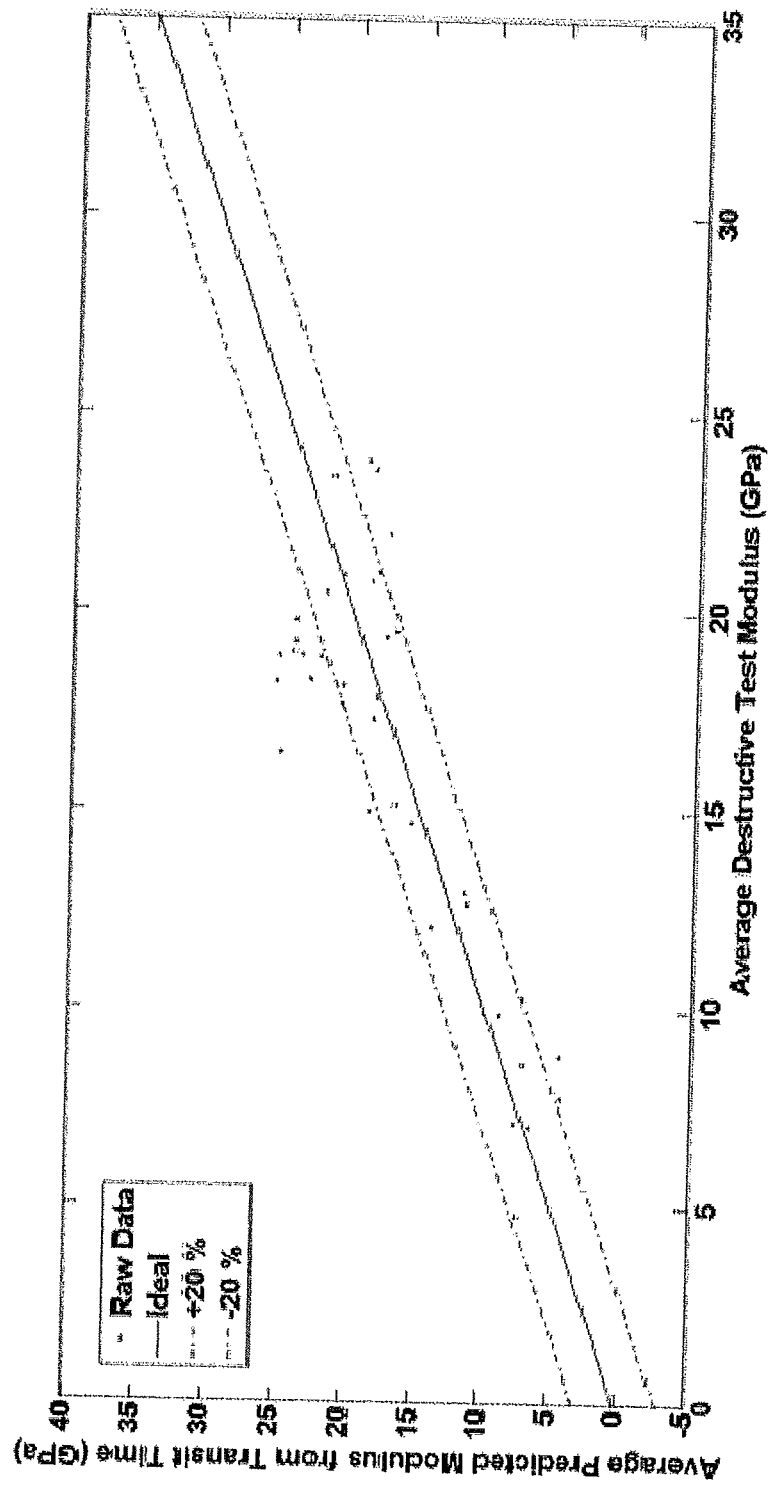

Table 9 outlines the average dimension of each sample. The results are shown in FIGS. 21A and 21B. It can be seen that the results of nondestructive tests and predictions are generally in agreement. Majority of the errors is within +/−20% as seen from FIGS. 21A and 21B. There are two results generated by the system for analyzing fiber reinforced composites, the first being Predicted Modulus for Transit Time, which calculates the modulus without knowledge or measurement of the samples thickness and the second being Predicted Modulus for Thickness which takes into account the measured thickness of the material.

TABLE 9

Comparison between destructive and non-destructive tests

| Samples | Width (m) | Thickness (m) | Span (m) | Fibre Type |
|---|---|---|---|---|
| N11A | 0.0303 | 0.006 | 0.0978 | Long Fibres |
| N11B | 0.0303 | 0.006 | 0.0978 | Long Fibres |
| TH149161A | 0.0302 | 0.0063 | 0.0978 | Long Fibres |
| TH149161B | 0.0302 | 0.0063 | 0.0978 | Long Fibres |
| TW105031A | 0.0303 | 0.0126 | 0.163 | Long Fibres |
| TW105031B | 0.0295 | 0.0113 | 0.163 | Long Fibres |
| TW121352A | 0.0298 | 0.0063 | 0.0978 | Long Fibres |
| TW121352B | 0.0298 | 0.0063 | 0.0978 | Long Fibres |
| TW149163A | 0.0303 | 0.0067 | 0.0978 | Long Fibres |
| TW149163B | 0.0303 | 0.0067 | 0.0978 | Long Fibres |
| YU15A | 0.0356 | 0.0268 | 0.4018 | Long Fibres |
| YU15B | 0.0355 | 0.0263 | 0.4018 | Long Fibres |
| YU16A | 0.0352 | 0.0261 | 0.4018 | Long Fibres |
| YU16B | 0.0352 | 0.0276 | 0.4018 | Long Fibres |
| YU17A | 0.0356 | 0.0278 | 0.4018 | Long Fibres |
| YU17B | 0.0347 | 0.0253 | 0.4018 | Long Fibres |
| YU18A | 0.0355 | 0.0268 | 0.4018 | Long Fibres |
| YU18B | 0.0352 | 0.026 | 0.4018 | Long Fibres |
| YU19A | 0.0356 | 0.0282 | 0.4018 | Long Fibres |
| YU19B | 0.0363 | 0.0258 | 0.4018 | Long Fibres |
| YU20B | 0.0359 | 0.027 | 0.4018 | Long Fibres |
| YU22A | 0.0386 | 0.008 | 0.0978 | Long Fibres |
| YU22B | 0.0389 | 0.0083 | 0.0978 | Long Fibres |
| YU23A | 0.039 | 0.005 | 0.0978 | Long Fibres |
| YU23B | 0.0378 | 0.0053 | 0.0978 | Long Fibres |
| YU24A | 0.0383 | 0.0082 | 0.0978 | Long Fibres |
| YU24B | 0.0389 | 0.0082 | 0.0978 | Long Fibres |
| YU26A | 0.0378 | 0.0042 | 0.0978 | Long Fibres |
| YU26B | 0.0385 | 0.0043 | 0.0978 | Long Fibres |
| YU27A | 0.038 | 0.0035 | 0.0978 | Long Fibres |
| YU27B | 0.0388 | 0.0037 | 0.0978 | Long Fibres |
| YU28A | 0.0375 | 0.0056 | 0.0978 | Long Fibres |
| YU28B | 0.0377 | 0.0051 | 0.0978 | Long Fibres |
| YU29A | 0.0381 | 0.006 | 0.0978 | Long Fibres |
| YU29B | 0.0379 | 0.006 | 0.0978 | Long Fibres |
| YU30A | 0.038 | 0.0054 | 0.0978 | Long Fibres |
| YU30B | 0.0378 | 0.0056 | 0.0978 | Long Fibres |
| YUS5A | 0.0365 | 0.0092 | 0.163 | Long Fibres |
| YUS5B | 0.0362 | 0.0095 | 0.163 | Long Fibres |
| YUS3A | 0.037 | 0.0105 | 0.163 | Chopped Fibres |
| YUS4A | 0.0383 | 0.0131 | 0.163 | Long Fibres |
| YUS7A | 0.0363 | 0.0105 | 0.163 | Chopped Fibres |
| YUS7B | 0.0361 | 0.0101 | 0.163 | Chopped Fibres |
| YUS1A | 0.0351 | 0.0087 | 0.0978 | Chopped Fibres |
| YUS1B | 0.0354 | 0.0089 | 0.0978 | Chopped Fibres |
| YUS2A | 0.0357 | 0.0088 | 0.155 | Chopped Fibres |
| YUS2B | 0.0357 | 0.0089 | 0.155 | Chopped Fibres |

The residual service life of the sample can be estimated if the theoretical modulus is known along with the time which the equipment has been in operation. By plotting the modulus versus time, the residual service life can be interpolated by a linear function. The following is an example calculation for sample #38. The theoretical modulus for this specimen was obtained using standard ignition test loss. This value is assumed to be the initial modulus at time zero. In practice, data sheets may be available to give more accurate information about the equipment itself. It is also assumed that the specimen was in service for 5 years.

The modulus of sample #38 was estimated to be 4.1 GPa and the theoretical modulus obtained from the ignition loss test is 5.53 GPa. By expressing both values as a percent of the initial value, the change in modulus results in a decrease of approximately 5.2%/year. Therefore in another 15 years the modulus will become 20% of its initial value which can be considered end of life.

The results from the nondestructive tests were found to be correlated with the prediction by the nondestructive test. Thus, the ultrasonic nondestructive test is intended to be a good indication of the modulus of material and the residual service life can then be inferred with knowledge of the design/theoretical modulus of the material. Also, it is noted that the thickness of the material need not be known to obtain accurate results. The thickness is inferred from the pulse transit time, which is intended to be another advantage of this method detailed herein. In practice, this may be considered an advantage for the ultrasonic nondestructive test method as an inspector can inspect the pressure vessels from outside without the need to shut down the plant to get the thickness information by drilling.

FRC pipes are on the rise due to their superior corrosion resistance, lightweight and high strength-to-weight ratio, which makes them attractive to be used in many industrial product applications. Prior knowledge of FRC piping defects, methods of inspection and FRC pipe material characterization prevents any unexpected failures. These defects affect the structural integrity of FRC pipes and their mechanical properties. Different methods and strategies for FRC pipe inspection can be used however embodiments of the ultrasonic testing and inspection method described herein are intended to provide advantages over other method in terms of reliability, portability (in field use) and easiness. The method in intended to use easily available instruments along with a short training cycle and highly automated data processing, thereby reducing inspector skill requirements.

In the preceding description, for purposes of explanation, numerous details are set forth in order to provide a thorough understanding of the embodiments. However, it will be apparent to one skilled in the art that these specific details may not be required. In other instances, well-known structures are shown in block diagram form in order not to obscure the understanding. For example, specific details are not provided as to whether the embodiments described herein are implemented as a software routine, hardware circuit, firmware, or a combination thereof.

Embodiments of the disclosure or portions thereof can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the description should not be limited by the particular embodiments set forth herein, but should be construed in a manner consistent with the specification as a whole.

Generally speaking, the description herein is intended to provide a method for non-destructive analysis of fiber reinforced composites, the method comprising: conducting ultrasonic analysis of the FRC; calculating a characteristic value based on the analysis; comparing the characteristic value based on the analysis to a baseline established for the characteristic value; and determining a percentage of design strength based on the comparison.

Generally speaking, there is also provided a system for non-destructive analysis of fiber reinforced composites (FRC), the system comprising: an ultrasonic module for sending and receiving ultrasonic signals in the FRC and generating ultrasonic signal data; an analysis module for processing the ultrasonic signal data; a calculation module for calculating a characteristic value based on the processing of the ultrasonic signal data; a comparison module for comparing the characteristic value to a baseline established for the characteristic value; a determining module for determining a percentage of design strength based on the comparison; and a processor for working with the other modules.

In some cases, the baseline for the characteristic value may be determined by linear regression analysis for a plurality of test results for the characteristic value.

In some cases, the percentage of design strength result may be used to determine a value for the remaining service life of the FRC.

I claim:

1. A system for analyzing fiber reinforced composite, the system comprising:
    an ultrasonic transmitter configured to provide ultrasonic pulses to the fiber reinforced composite;
    an ultrasonic receiver configured to receive ultrasonic signal data related to the ultrasonic pulses;
    a filter module configured to filter the ultrasonic signal data to extract relevant data from the ultrasonic signal data and remove data that is not associated with a material being tested in order to determine a net response of the fiber reinforced composite from the ultrasonic pulses;
    a signal processing module configured to process the net response of the filtered ultrasonic signal data;
    an analysis module configured to analyze the processed net response of the filtered ultrasonic signal data to determine a result reflecting a condition of the material being tested; and
    an output module configured to output the result.

2. A system according to claim 1, wherein the analysis module is configured to analyze the processed ultrasonic signal data to determine the result by:
    calculating a characteristic value based on the ultrasonic signal data;
    comparing the characteristic value to a baseline established for the characteristic value; and
    determining the result based on the comparison.

3. A system according to claim 1, further comprising a memory component configured to store ultrasonic signal data and baseline for characteristic values.

4. A system according to claim 1, wherein the relevant data comprises data associated with the material being tested and the removed data comprises data associated with the ultrasonic transmitter and the ultrasonic receiver.

5. A system according to claim 1, wherein the relevant data comprises a magnitude of a reflection from the opposite surface of the fiber reinforced composite.

6. A system according to claim 1, wherein the output module is further configured to output a projection of a time remaining prior to a predetermined threshold value is reached.

7. A system according to claim 6 wherein the predetermined threshold value is a value related to a replacement requirement.

8. A system of claim 1 wherein the output module is further configured to output data related to a strength level of a bonding at joins of the fiber reinforced composite.

9. A system according to claim 1, wherein the result is a percentage of design stiffness.

10. A method for analyzing fiberglass reinforced polymer, the method comprising:
    taking ultrasonic signal data from the fiber reinforced composite;
    receiving the ultrasonic signal data, at an ultrasonic receiver;
    filtering the ultrasonic signal data, at a filter module, to extract relevant data from the ultrasonic signal data and remove data that is not associated with a material being tested in order to determine a net response of the fiber reinforced composite from the ultrasonic pulses;
    processing the net response of the filtered ultrasonic signal data, at a signal processing module;

analyzing the processed net response of the filtered ultrasonic signal data, at an analysis module, to determine a result reflecting a condition of the material being tested; and displaying the result, at an output module.

11. A method of claim 10, wherein the analyzing the processed ultrasonic signal data, at an analysis module, to determine the result comprises:
calculating a characteristic value based on the ultrasonic signal data;
comparing the characteristic value to a baseline established for the characteristic value; and
determining the result based on the comparison.

12. A method according to claim 10, further comprising storing the ultrasonic signal data and baseline for characteristic values at a memory component.

13. A method according to claim 10, wherein the relevant data comprises data associated with the material being tested and the removed data comprises data associated with the ultrasonic transmitter and the ultrasonic receiver.

14. A method according to claim 10 wherein the relevant data comprises includes a magnitude of a reflection from the opposite surface of the fiber reinforced composite.

15. A method according to claim 10, further comprising displaying a projection of a time remaining prior to a predetermined threshold value is reached.

16. A method according to claim 15, wherein the predetermined threshold value is a value related to a replacement requirement.

17. A method according to claim 10, further comprising displaying data related to a strength level of a bonding at joins of the fiber reinforced composite.

18. A method according to claim 10, wherein the result is a percentage of design stiffness.

* * * * *